United States Patent
Rothenberg et al.

(10) Patent No.: US 10,918,801 B2
(45) Date of Patent: Feb. 16, 2021

(54) CAPS FOR INTEGRATED FILL AND INJECT OF SAFETY NEEDLE DEVICES

(71) Applicant: Becton, Dickinson and Company, Franklin Lakes, NJ (US)

(72) Inventors: Ashley Rachel Rothenberg, Morris Plains, NJ (US); Theodore Mosler, Raleigh, NC (US); Laurie Sanders, Glen Ridge, NJ (US); Edward P. Browka, Oneida, NY (US); Peter Smith, Cary, NC (US); Eli B. Nichols, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 352 days.

(21) Appl. No.: 15/838,461

(22) Filed: Dec. 12, 2017

(65) Prior Publication Data
US 2018/0161514 A1    Jun. 14, 2018

Related U.S. Application Data

(60) Provisional application No. 62/433,526, filed on Dec. 13, 2016.

(51) Int. Cl.
*A61M 5/32*  (2006.01)
*A61M 5/20*  (2006.01)
(Continued)

(52) U.S. Cl.
CPC ......... *A61M 5/3202* (2013.01); *A61B 5/1444* (2013.01); *A61J 1/201* (2015.05);
(Continued)

(58) Field of Classification Search
CPC .. A61M 5/326; A61M 5/3272; A61M 5/3202; A61M 5/1782; A61M 2005/3267; A61M 2005/3247; A61B 5/1444
See application file for complete search history.

(56) References Cited

U.S. PATENT DOCUMENTS

| 4,711,363 A | 12/1987 | Marino |
| 4,738,376 A | 4/1988 | Markus |

(Continued)

FOREIGN PATENT DOCUMENTS

| CA | 2803761 A1 | 12/2011 |
| CN | 103079610 A | 5/2013 |

(Continued)

OTHER PUBLICATIONS

PCT International Search Report and Written Opinion in PCT/US2017/065956 dated Mar. 5, 2018, 14 pages.

(Continued)

*Primary Examiner* — Laura A Bouchelle
*Assistant Examiner* — Anh Bui
(74) *Attorney, Agent, or Firm* — Servilla Whitney LLC

(57) ABSTRACT

Drug delivery safety devices comprise a safety needle device comprising a needle hub, a needle cannula, and a safety feature; and a cap comprising a cap body having a proximal end attached to the safety needle device and a distal end having an access opening that is in fluid communication with the needle cannula. The safety needle device allow for an integrated device for both filling and injection that do not interfere with passive safety features. The caps may have a fill feature that engages with a safety feature of the safety needle device to keep it in a fill state.

15 Claims, 21 Drawing Sheets

(51) Int. Cl.
  *A61M 5/00* (2006.01)
  *A61M 5/50* (2006.01)
  *A61J 1/20* (2006.01)
  *A61M 5/178* (2006.01)
  *A61B 5/15* (2006.01)

(52) U.S. Cl.
  CPC .......... *A61J 1/2048* (2015.05); *A61J 1/2068* (2015.05); *A61J 1/2096* (2013.01); *A61M 5/002* (2013.01); *A61M 5/1782* (2013.01); *A61M 5/2033* (2013.01); *A61M 5/321* (2013.01); *A61M 5/326* (2013.01); *A61M 5/3243* (2013.01); *A61M 5/3272* (2013.01); *A61M 5/50* (2013.01); *A61M 5/504* (2013.01); *A61M 2005/325* (2013.01); *A61M 2005/3247* (2013.01); *A61M 2005/3267* (2013.01)

(56) References Cited

U.S. PATENT DOCUMENTS

| | | | |
|---|---|---|---|
| 4,795,432 | A | 1/1989 | Karczmer |
| 4,813,940 | A | 3/1989 | Parry |
| 4,950,250 | A | 8/1990 | Haber |
| 5,395,347 | A | 3/1995 | Blecher |
| 5,496,288 | A | 3/1996 | Sweeny |
| 5,591,138 | A | 1/1997 | Vaillancourt |
| 5,676,406 | A | 10/1997 | Simmons et al. |
| 5,688,241 | A | 11/1997 | Asbaghi |
| 5,984,899 | A | 11/1999 | D'Alessio |
| RE36,885 | E | 9/2000 | Blecher |
| 6,632,199 | B1 | 10/2003 | Tucker et al. |
| 6,884,237 | B2 | 4/2005 | Asbaghi |
| 6,926,697 | B2 | 8/2005 | Malenchek |
| 7,361,159 | B2 | 4/2008 | Fiser |
| 7,513,888 | B2 | 4/2009 | Sircom |
| 7,811,261 | B2 | 10/2010 | Rubinstein |
| 8,062,265 | B2 | 11/2011 | Millerd |
| 8,162,882 | B2 | 4/2012 | Rubinstein |
| 8,303,541 | B2 | 11/2012 | Chun |
| 8,333,738 | B2 | 12/2012 | Millerd |
| 8,388,894 | B2 | 3/2013 | Colantonio |
| 8,439,870 | B2 | 5/2013 | Moyer |
| 8,496,627 | B2 | 7/2013 | Chelak |
| 8,636,688 | B2 | 1/2014 | Shaw |
| 8,636,703 | B2 | 1/2014 | Foshee |
| 8,647,307 | B2 | 2/2014 | Gratwohl |
| 8,663,129 | B2 | 3/2014 | Allen |
| 8,721,627 | B2 | 5/2014 | Alpert et al. |
| 8,747,355 | B2 | 6/2014 | Rubinstein |
| 8,784,388 | B2 | 7/2014 | Charles et al. |
| 8,827,961 | B2 | 9/2014 | Emmott |
| 8,968,241 | B2 | 3/2015 | Liversidge |
| 8,979,794 | B2 | 3/2015 | Chevallier |
| 9,050,416 | B2 | 6/2015 | Feret |
| 9,061,106 | B2 | 6/2015 | Roberts |
| 9,067,024 | B2 | 6/2015 | Roberts |
| 9,186,466 | B2 | 11/2015 | Zachek |
| 9,192,449 | B2 | 11/2015 | Kerr et al. |
| 9,352,099 | B2 | 5/2016 | Roberts |
| 9,352,100 | B2 | 5/2016 | Ward |
| 9,352,101 | B2 | 5/2016 | Roberts |
| 9,370,327 | B2 | 6/2016 | Teoh |
| 9,408,632 | B2 | 8/2016 | Erskine |
| 9,445,760 | B2 | 9/2016 | Allen |
| 9,694,140 | B2 | 7/2017 | Rubinstein |
| 9,848,810 | B2 | 12/2017 | Allen |
| 10,099,048 | B2 | 10/2018 | Chiu et al. |
| 10,166,381 | B2 | 1/2019 | Gardner et al. |
| 2004/0039341 | A1 | 2/2004 | Ranalletta |
| 2007/0060904 | A1* | 3/2007 | Vedrine ................ A61J 1/2096 604/411 |
| 2010/0049170 | A1 | 2/2010 | Solomon et al. |
| 2010/0298770 | A1 | 11/2010 | Rubinstein |
| 2011/0046603 | A1 | 2/2011 | Felsovalyi et al. |
| 2011/0054440 | A1 | 3/2011 | Lewis |
| 2011/0264037 | A1 | 10/2011 | Foshee et al. |
| 2012/0039764 | A1 | 2/2012 | Solomon et al. |
| 2012/0123386 | A1 | 5/2012 | Tsals |
| 2012/0302997 | A1 | 11/2012 | Gardner et al. |
| 2013/0085474 | A1 | 4/2013 | Charles et al. |
| 2013/0197485 | A1 | 8/2013 | Gardner et al. |
| 2013/0338644 | A1 | 8/2013 | Solomon et al. |
| 2014/0052074 | A1 | 2/2014 | Tekeste |
| 2014/0135706 | A1 | 5/2014 | Rubinstein |
| 2014/0228770 | A1 | 8/2014 | Ward |
| 2014/0364803 | A1 | 12/2014 | Rubinstein |
| 2015/0094659 | A1 | 4/2015 | Schraga |
| 2015/0094666 | A1* | 4/2015 | Bates ................ A61M 5/1782 604/197 |
| 2015/0182704 | A1 | 7/2015 | Chevallier |
| 2015/0190580 | A1 | 7/2015 | Imai |
| 2015/0190586 | A1 | 7/2015 | Takemoto |
| 2017/0203092 | A1 | 7/2017 | Ryan et al. |
| 2018/0200145 | A1 | 7/2018 | Sanders et al. |
| 2018/0256883 | A1 | 9/2018 | Follman et al. |
| 2019/0234540 | A1 | 8/2019 | Marici et al. |

FOREIGN PATENT DOCUMENTS

| | | |
|---|---|---|
| DE | 20017013 U1 | 12/2000 |
| DE | 10247963 A1 | 5/2004 |
| EP | 2606930 A1 | 6/2013 |
| EP | 2832391 B1 | 2/2015 |
| EP | 2585146 B1 | 3/2017 |
| EP | 3275490 A1 | 1/2018 |
| GB | 2518646 A | 4/2015 |
| JP | 2013529973 A | 7/2013 |
| MX | 2013/000081 | 3/2013 |
| MX | 349289 B | 7/2017 |
| WO | 200024442 A1 | 5/2000 |
| WO | 200224551 A1 | 3/2002 |
| WO | 2012/013587 A1 | 2/2012 |
| WO | 2015127285 A1 | 8/2015 |
| WO | 2018106508 A1 | 6/2018 |
| WO | 2019152482 A1 | 8/2019 |

OTHER PUBLICATIONS

PCT International Search Report and Written Opinion in PCT/US2020/015535 dated May 4, 2020, 13 pages.
Non-Final Office Action in U.S. Appl. No. 16/253,683, dated Jun. 26, 2020, 9 pages.
Non-Final Office Action in U.S. Appl. No. 16/254,747, dated Aug. 20, 2020, 14 pages.
PCT International Search Report and Written Opinion in PCT/US2020/044942 dated Oct. 16, 2020, 15 pages.
PCT International Search Report and Written Opinion in PCT/US2020/041312 dated Oct. 19, 2020, 11 pages.
PCT International Search Report and Written Opinion in PCT/US2020/044951 dated Oct. 14, 2020, 14 pages.
PCT International Search Report and Written Opinion in PCT/US2020/041097 dated Oct. 27, 2020, 18 pages.
Non-Final Office Action in U.S. Appl. No. 16/378,015, dated Oct. 30, 2020, 18 pages.

* cited by examiner

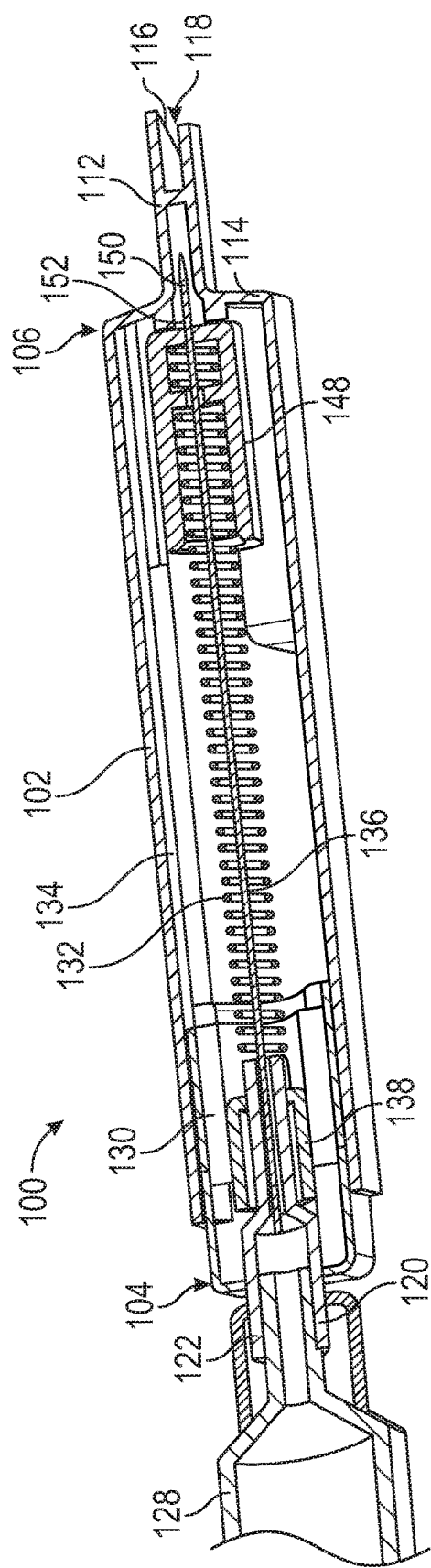
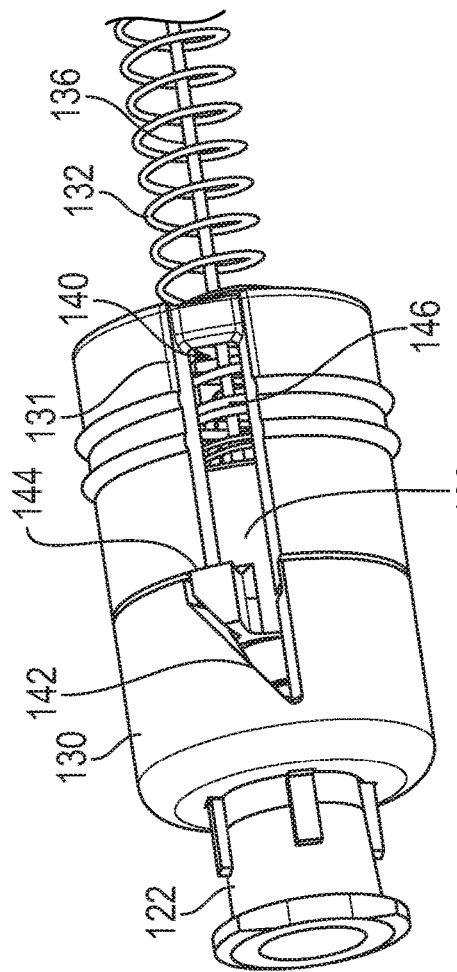
FIG. 4
FIG. 5

CAPS FOR INTEGRATED FILL AND INJECT OF SAFETY NEEDLE DEVICES

CROSS-REFERENCE TO RELATED APPLICATIONS

This application claims priority under 35 U.S.C. § 119(e) to U.S. Provisional Application No. 62/433,526, filed Dec. 13, 2016, the disclosure of which is incorporated herein by reference in its entirety.

TECHNICAL FIELD

The present disclosure relates generally to drug delivery safety devices. Specifically, caps for safety needle devices allow for integrated filling and injection.

BACKGROUND

Accidental needle sticks with a used needle can transmit disease. Needle assemblies were developed to include needle shields, which are manually telescoped or rotated over a needle cannula after use. This procedure often requires the healthcare worker to hold the syringe barrel in one hand and the shield in the other and assemble the two before risk of needle stick is eliminated. Some safety needle devices offer passive safety features to provide post-injection needle shielding without additional intervention by the user. Passive safety features are activated in many kinds of ways but generally involve a mechanical structure to lock a needle in place or cover it.

For drug delivery, a syringe is connected to a needle for filling from a fluid supply or fluid holding device, e.g., a vial, and subsequent injection to a patient. A fill state generally of a safety needle device allows for multiple fills, which do not activate the passive safety feature. For some safety needle devices, there is a risk that injection occurs with the device in a fill state, which may result in the passive safety device not activating. After filling, there is an inject state of the safety needle devices in which the passive safety feature will be activated upon completion of the injection.

There is a need to prevent misuse of safety needle devices. There is also a need for caps for safety needle devices that allow for an integrated device for both filling and injection that do not interfere with passive safety features.

SUMMARY

Provided are caps for safety needle devices, which allow for an integrated device for both filling and injection that do not interfere with passive safety features. The caps have an access opening that is in fluid communication with a needle cannula. The access opening may comprise an access protrusion extending from a distal end of the cap. Exemplary such caps include, but are not limited to: a spike cap, which includes a spike, typically plastic, as the access protrusion for accessing a fluid supply; and a blunt fill needle cap, which includes a blunt fill cannula, typically metal, secured in the access protrusion. The caps may have a fill feature that engages with a safety feature of the safety needle device to keep it in a fill state.

Various embodiments are listed below. It will be understood that the embodiments listed below may be combined not only as listed below, but in other suitable combinations in accordance with the scope of the disclosure.

In an aspect, a drug delivery safety device comprises: a safety needle device comprising a needle hub, a needle cannula, and a safety feature; and a cap comprising a cap body having a proximal end attached to the safety needle device and a distal end having an access opening that is in fluid communication with the needle cannula.

In another aspect, a safety needle device comprising a needle hub, a needle cannula, and a safety feature; and a cap comprising a cap body having a proximal end attached to the safety needle device, an access opening that is in fluid communication with the needle cannula, and a fill feature that maintains the safety needle device in a fill state.

Other aspects include methods of drug delivery comprises: obtaining any drug delivery safety device disclosed herein; attaching a syringe to the drug delivery safety device; inserting the access protrusion of the cap into a fluid supply; filling the syringe with a fluid; removing the cap; and injecting the fluid into a patient.

BRIEF DESCRIPTION OF THE DRAWINGS

FIG. 4 is a cross-section view of the drug delivery safety device according to FIG. 1 assembled with a syringe;

FIG. 5 provides a close-up perspective view of a proximal end of a safety needle device as included in FIG. 4;

DETAILED DESCRIPTION

Figure 1:
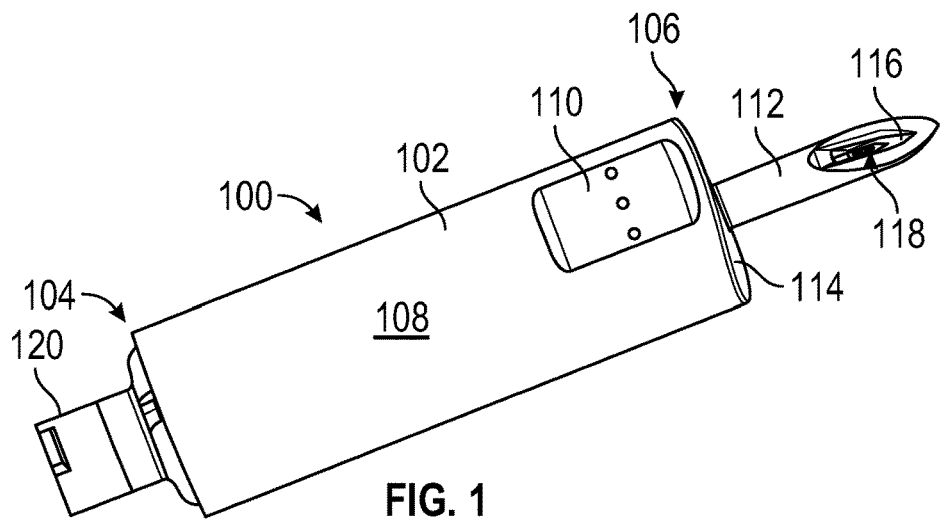
FIG. 1 is a perspective view of a drug delivery safety device according to an embodiment.

Before describing several exemplary embodiments, it is to be understood that the disclosure is not limited to the details of construction or process steps set forth in the following description. The disclosure is capable of other embodiments and of being practiced or being carried out in various ways.

Caps for safety needle devices are configured for removable attachment to the safety needle devices. The caps allow for an integrated drug delivery safety device for both filling and injecting. A safety needle device has one or more safety features, which may be referred to as a passive lockout safety. The caps allow for keeping the safety needle devices in a fill state. Upon removal of the caps, the safety needle devices are in an injection state. Assemblies herein facilitate "3 Choice" Passive Safety Device Functional Architecture which allows a user to Fill and Inject with the same device. Misuse by injection when the safety needle is in its fill state is also minimized and/or avoided. The device in fill state is intended to prevent the user from injecting a patient, for example it would be very difficult, painful, and against convention to use a blunt fill, plastic spike, or vial access device to deliver to a patient. The caps disclosed here may restrain the passive lockout safety, which is permissible because while they do this they add these other impediments to injection. With specific regard to spike caps and blunt needle fill caps, users are not limited in accessing vials including those of varying depths.

Caps

Caps comprises a cap body having a proximal end attached to a safety needle device and an access opening that is in fluid communication with a needle cannula of the safety needle device. The access opening may comprise an access protrusion extending from a distal end of the cap. Caps having access protrusions include spike caps and blunt fill needle caps. The access protrusions may have a vent lumen to allow for pressure equalization in the vial (allows for large and or withdrawals without a pre-air bolus withdrawals). The vent lumen may have a filter to prevent vial contamination.

A spike cap includes a spike, typically plastic. The spike may be designed to include internal features, straws, and/or faces to facilitate manufacture and fill, minimize drug holdup, and to protect the needle cannula of the safety needle device. A blunt fill needle cap, which includes a blunt fill cannula, typically metal, secured in the access protrusion. The blunt fill cannula may be blunt and metal, a single bevel, a pencil tip with side port, fully sharp, or any desired tip geometry.

Caps may be fabricated from suitable medical grade materials including polymers or metals. Preferably the caps are injection-molded using a thermoplastic and/or thermoplastic elastomer (TPE). Septums for inside the cap may be fabricated from a suitable elastomer. Finger grips for an outside surface of the cap can be formed from the same elastomer as the septum. Caps may be fabricated as a "two shot" molded part.

Caps may have fill features to keep them in a fill state. The fill features are a characteristic of the cap including a dimension or a structure. A dimension of the cap, e.g., its length, may allow no restrictions on needle penetration thereby keeping the needle device in a fill state. As a non-limiting first example, an initial length of a needle cannula of the underlying safety needle device is enough to penetrate the septum of the cap and allow fluid to flow. A second non-limiting example is that a sleeve of the underlying device is compressed to a length when the cap is on that is less than the activation distance. A structure of the cap may engage with a safety feature of the safety needle device. A structure of the cap may be on its inside surface, designed to contacts a safety feature of the safety needle device. Such structures may protrude from the inside surface, comprising, for example, ribs, ledges, posts, lugs, angled cams, and the like; and/or the structures may be below the inside surface, including, but not being limited to, grooves, channels, tracks, and the like; and/or the structures may be additional components contained in the cap body such as tubes. Spike caps and blunt fill needle caps optionally have fill features, depending on the underlying safety needle device.

The cap engages with a portion of the safety needle device by methods including but not limited to: snap-fit, rotatably-fit, press-fit. The cap may be removed by pulling, quarter turning, or squeezing to disengage. For an embodiment for squeezing to disengage, a latch on the cap may be present that requires only non-axial force.

In one or more embodiments, the safety feature is an activation latch, found for example in a stored energy latch safety needle device or in a front end trigger safety needle device, and the fill feature is a rib that keeps the safety feature disengaged.

In one or more embodiments, the safety feature is a clip, found for example in a linear distance trigger safety needle device, and the fill feature is a tube or a rib or a ledge that keeps arms of the clip open.

In one or more embodiments, the safety feature is a guide element of a housing body, found for example in a tube-in-tube safety needle device, and the fill feature is the dimension of the cap which allows for multiple fills without activating the safety device.

Safety Needle Devices

Any suitable needle devices comprising a safety feature may be used in conjunction with the caps disclosed herein. Exemplary safety needle devices include, but are not limited to, those described in commonly owned, co-filed internal reference numbers P-15379@ (tube-in-tube), P-15380@ (stored energy latch), and P-15385@ (collapsible housings, which include rotating force trigger, linear distance trigger, and front end trigger), the disclosures of which are incorporated herein by reference in their entireties. Types of safety features vary in structure and mechanics but in general, safety needle devices have a fill state and an inject state.

3 Choice Architecture

To start, a product comes packaged in a safe state in which the needle is covered and prevents needle stick injury (NSI). This can be in the form of a hard-pack or in a blister with a separate cap. At this point the user makes the first choice—Fill (access a vial to fill a syringe or transfer fluids) or Inject (insert the needle into a patient to deliver medication)—and they actively change the device to that state. Assuming the user chooses to Fill, once they complete filling, they now make the second choice, do I fill again (perform another vial access), move the product to an inject state, or more the product to a transport state. Note that each of these choices requires an active motion by the user. Assuming the user chooses to move the product to the transport state, they now placing it into a safe state that could prevent NSI's. Following transportation, the user then needs to make the third choice—actively change the product to then inject state. Once in the inject state, within approximately the first 5 mm or less of the needle penetrating the patient's skin (or other medium) the device will automatically lock out—thereby defining passive safety.

Whenever the device is in a "fill state" it is in a state that allows for potential needle stick injury and when the needle enters into a vial (or other medium) and then exits, it does not lock. This means that a user could access a vial to fill an infinite number of times. Similarly, whenever the device is in an "inject state" it is in a state that also allows for potential needle stick injury. However, once the needle enters into a patient (or other medium) then exits it automatically locks after 1 time.

A user can move the Inject State at any point in the process. This means that the user can go from state to inject, fill to inject, or transport to inject as indicated above. In order to change states in a 3 Choice functional architecture, a combination of cap and safety needle device may be used including but not limited to the following embodiments.

Flip Cap—A flip cap could be used to change states between Start, Fill, Transport, and Inject. The flip cap would start closed, could be flipped open to fill, could be flipped closed to transport, and could be removed prior to injection to achieve the injection state. However, unlike devices that limit the distance that the needle can penetrate the vial in order to prevent passive safety device activation, the flip cap herein does not require limiting the distance of needle penetration. This solves the problem associated with devices that limit needle penetration distance and the trade-off regarding penetration depth in the fill state and the inject state. For example, in a device that limits needle penetration, a user may only have approximately 15 mm or less needle length to access the vial and similarly the device does not lock out in the patient skin until a depth of 15 mm or greater is achieved. With the flip cap disclosed herein, when the cap is on the full needle length can be used without locking out and when the cap is off the needle locks out almost immediately after entry in to the patient's skin (approximately 5 mm or less). Mechanisms that can use this flip cap include stored energy latch, rotating force trigger, linear distance trigger, and front end trigger.

Double Caps—A double cap can be used to change states between start, fill, transport, and inject. To start the product comes with both caps on. To fill remove the first "mini-cap." To transport, re-attach the "mini-cap." To inject, remove the "large-cap" contains the "mini-cap." (Note: The large cap can also be removed however on its own once fill is completed if a user wants to go directly from fill to inject) Like with the flip cap above the double cap does not work on limiting distance. Therefore, the full needle can be used for filling if desired and the once the caps are both removed, lock out occurs almost immediately after the needle enters the patient's skin (approximately 5 mm or less). Mechanisms developed today that can use this double cap include stored energy latch, rotating force trigger, linear distance trigger, and front end trigger.

Alternate Caps—Other Alternate caps also are suitable for 3 Choice. These include the Clothes Pin Cap, Twist Cap, Basket Cap with Flex Arms, Spikey Cap, Collet Cap, and Cap with Grip Arms as shown in FIGS. 27-37 discussed below. Alternate caps can work with stored energy latch, rotating force trigger, linear distance trigger, and front end trigger.

Spike Cap or Blunt Fill Needle Cap-Like the double cap, the spike cap or blunt fill needle cap could come packaged with or without a "mini-cap." (If no "mini-cap" then cap removal and re-capping would not be required.) A spike cap or blunt fill needle cap packaged with a mini-cap, would involve removing the mini-cap to fill, replacing the mini-cap to transport, and remove the spike cap or blunt fill needle cap to inject. However, unlike the double cap the spike cap and blunt fill needle cap would have the added benefits of (1) protecting the needle tip used from injection from dulling and (2) deterring a user from injecting with the device in a fill state as clinicians are highly unlikely to try to inject a patient with a plastic molded spike or a or blunt fill needle. This also helps to drive compliance with using the device correctly and makes it more intuitive to learn.

Figure 2:
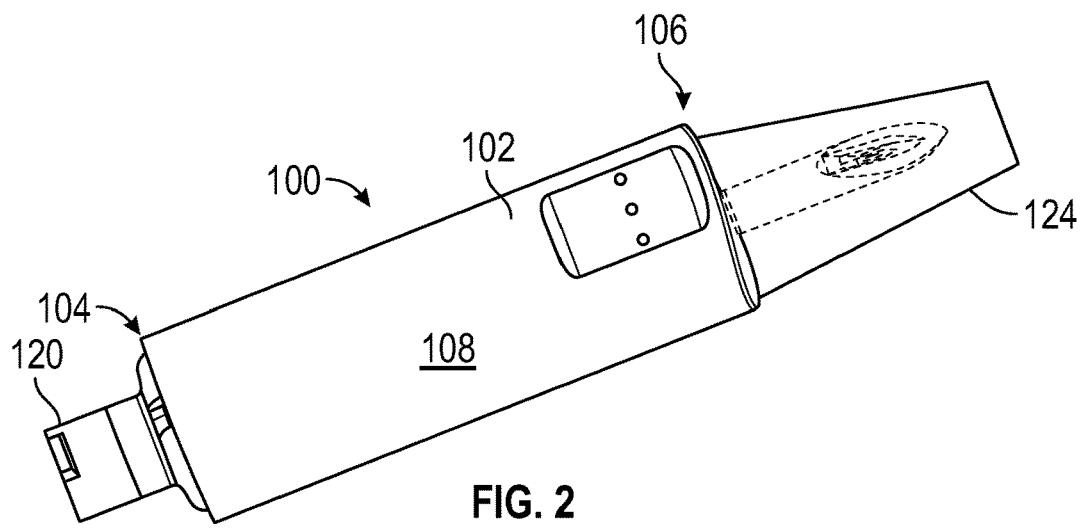
FIG. 2 is a perspective view of the drug delivery safety device according to FIG. 1 further including a tip cap.

Turning to the figures, FIGS. 1-2 are perspective views of a drug delivery safety device according to an embodiment. Drug delivery device 100 comprises a cap 102 and a safety needle device 120. The cap 102 removably attaches to a portion of the safety needle device 120 at a proximal end 104 of the cap 102. The cap 102 engages with a portion of the safety needle device 120 by methods including but not limited to: snap-fit, rotatably-fit, press-fit. The cap may be removed by pulling, quarter turning, or squeezing to release.

At a distal end 106 of the cap 102, there is a finger hilt 110, which also provides a grip area. An access protrusion 112 extends from a shoulder 114 of the cap 102. The shoulder 114 acts as a spike stop against a vial. There is a beveled tip 116 having an opening 118 at the end of the access protrusion 112. The drug delivery safety device 100 may further include a tip cap 124 as shown in FIG. 2. The tip cap 124 may snap-fit, rotatably-fit, or press-fit to the distal end 106 of the cap 102. The cap 102 of this embodiment may be referred to as a spike cap.

Figure 3:
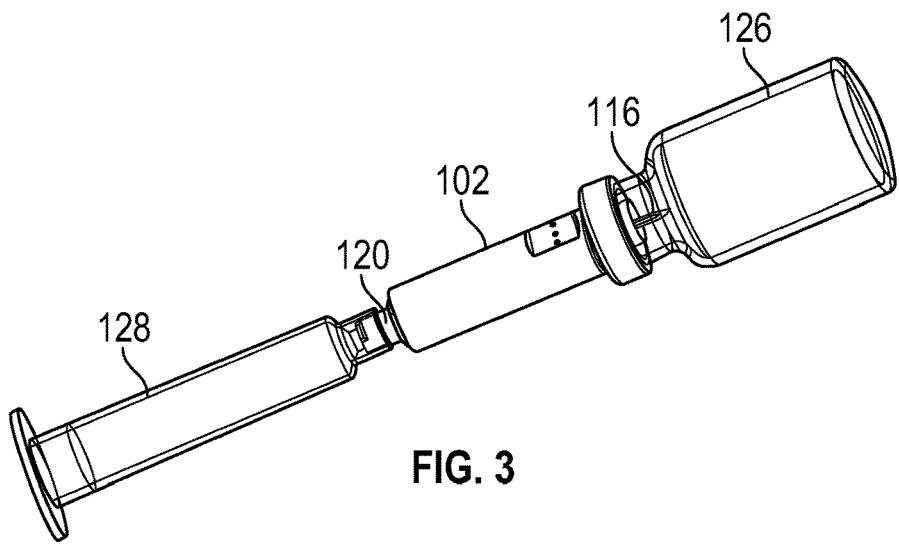
FIG. 3 is a perspective view of the drug delivery safety device according to FIG. 1 being used to fill a syringe from a vial.

FIG. 3 shows the beveled tip 116 of the spike cap 102 upon insertion into a vial 126. A syringe 128 is attached to a needle hub of the safety needle device 120 is filled with fluid from the vial 126. Low force (e.g., 0 lbs) is needed to push vial off of the spike cap.

An exemplary safety needle device is referred to herein as a "rotating force trigger," which is shown in cross-section in combination with a syringe and spike cap in FIG. 4. A close-up perspective view of a proximal end of the "rotating force trigger" is shown in FIG. 5. The "rotating force trigger" embodiment contains one or more safety features in the form of its rotating cam, lock clip, and/or device cap. In FIGS. 4-5, the rotating force trigger drug delivery safety device 120 comprises a needle hub 122 for attachment of the drug delivery safety device 120 to a syringe 128; needle hub 122 has an attached needle cannula 136. A device body 130, which engages needle hub 122, encloses a rotating cam 138. Rotating cam 138 engages body 130 through a slot 140 in a sidewall 131 of body 130. As shown in more detail in FIG. 5, slot 140 comprises three segments: a proximal angled lead ramp 142, a ledge 144 at the distal end of the angled lead ramp for seating the rotating cam, and an axial slot portion 146 distal to the ledge.

Needle cannula 136 is surrounded by a flexible housing 134 which connects rotating cam 138 to a lock clip (not shown) near the distal end of needle cannula 136 such that needle cannula 136 is substantially covered by the flexible housing but a distal tip 150 of the needle cannula 136 is exposed. The passive shielding system includes a trigger mechanism comprising a first spring 132 which connects rotating cam 138 to the lock clip and a second spring (not shown) in body 130 extending from rotating cam 138 proximally toward needle hub 122. First spring 132 biases lock clip distally and second spring biases rotating cam 138 distally. The lock clip may be housed in a device cap 148 which is attached to flexible housing 134.

The distal tip 150 of the needle cannula 136 goes through a septum 152 upon entering a channel of the access protrusion 112. Septum 152 is located at the distal end of the cap 102. Its proximity to the tip of the access protrusion 112 (e.g., plastic spike) allows for the septum 152 to be only penetrated at the time of use, by pulling the cap 102 proximally toward the hub 122. This may improve sealing of the septum and allow for less elastomer to be used. Also this septum location may allow for less residual drug holdup in the device.

Figure 6:
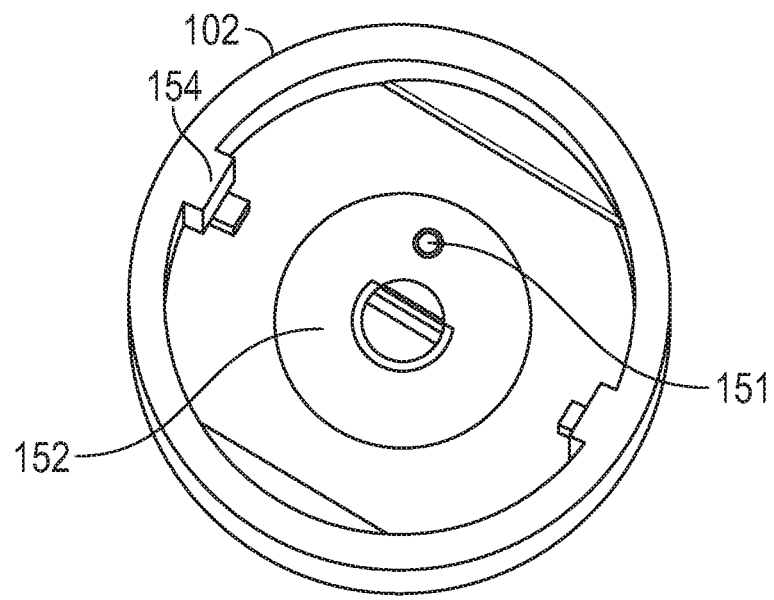
FIG. 6 is an interior view from a proximal end of a spike cap as included in FIG. 1 to a distal end of the cap.
Figure 7:
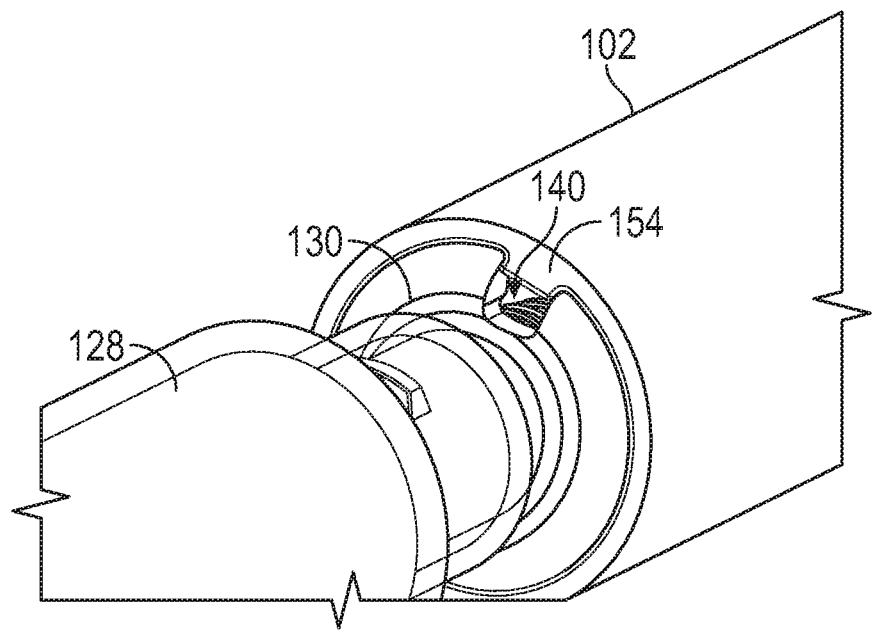
FIG. 7 illustrates a schematic view of an exemplary fill feature engaged with an exemplary safety feature.

FIG. 6 is an interior view from the proximal end of the spike cap 102 to a distal end of the cap, showing the septum 152 and fill feature 154. Fill feature 154 is a rib on an interior surface of the cap 102. Fill feature 154 interacts with the rotating cam 138 safety feature of the "rotating force trigger" embodiment upon assembly by residing in the slot 140 to keep it in a fill state. An optional lumen vent 151 allows for pressure equalization in the vial (allows for large and or withdrawals without a pre-air bolus withdrawals). FIG. 7 illustrates the syringe 128 assembled with a slotted safety needle device where fill feature 154 (e.g., a rib) of spike cap 102 resides in slot 140 of body 130.

Figure 8:
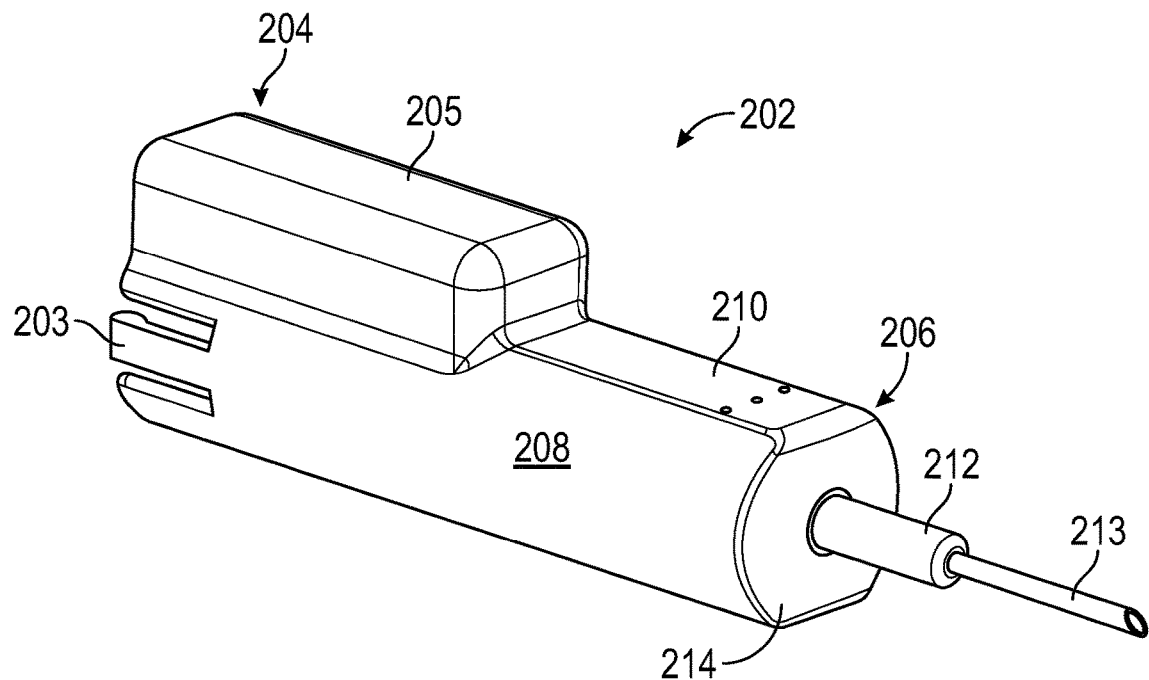
FIG. 8 provides a perspective view of a blunt fill needle cap according to an embodiment.

FIG. 8 provides a perspective view of a blunt fill needle cap 202 according to an embodiment. At a proximal end 204, there are one or more clips 203 for engaging with a portion of a needle safety device. The cap body 208 has a recess 205 for accommodating an underlying needle safety device having an activation latch. At a distal end 206 of the cap 202, there is a finger hilt 210. An access protrusion 212 extends from a shoulder 214 of the cap 202. A cap cannula 213 extends from a distal end of the access protrusion 212. A mini-cap may be provided for the cap cannula 213. The cap 202 of this embodiment may be referred to as a blunt needle fill cap.

Figure 9:
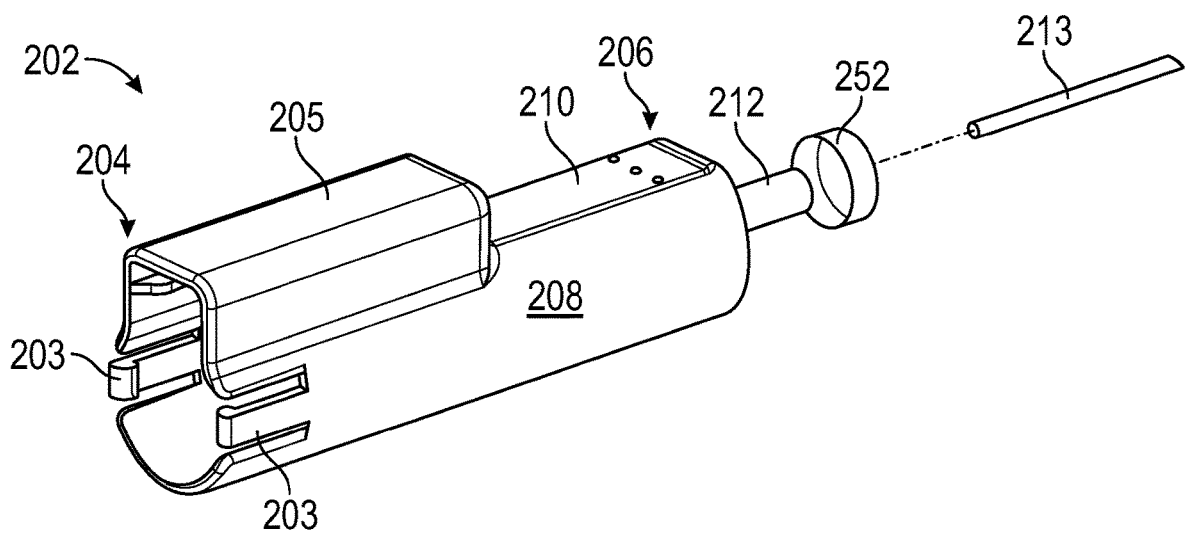
FIG. 9 provides an exploded perspective view of the blunt fill needle cap of FIG. 7.
Figure 10:
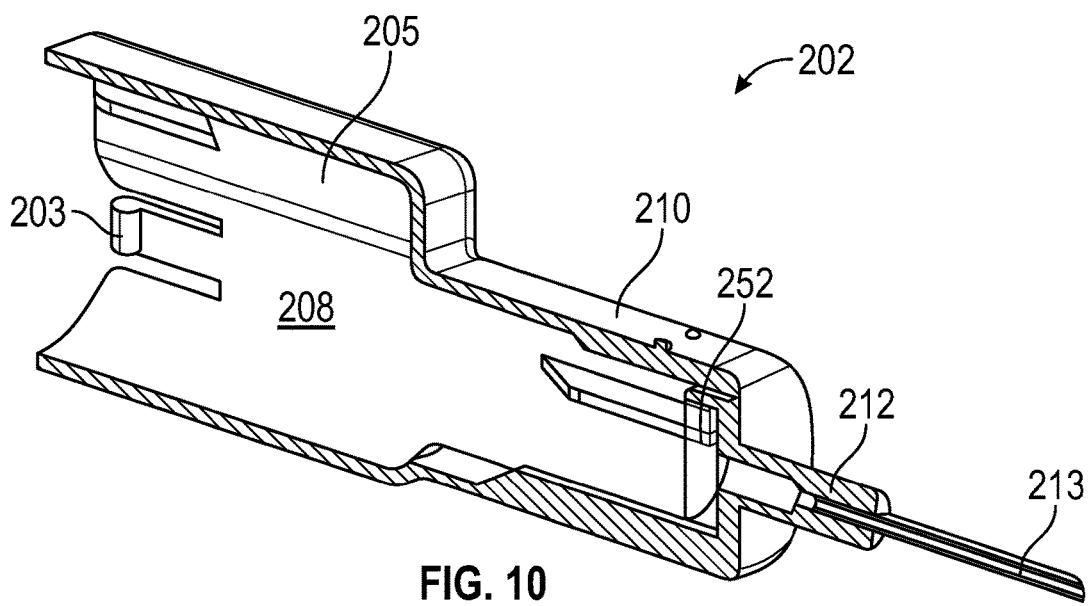
FIG. 10 provides a cross-section view of the blunt fill needle cap of FIG. 8.

FIG. 9 provides an exploded perspective view of the blunt fill needle cap 202 of FIG. 8 comprising the cap body 208, which has the recess 205 and clips 203, a septum 252, and the cap cannula 213. FIG. 10 provides a cross-section view of the blunt fill needle cap 202 of FIG. 8 as assembled: comprising the cap body 208, which has the recess 205 and clip 203, a septum 252, which resides in the distal end 206 of the cap 202, and the cap cannula 213, which resides in the access protrusion 212. A seal may be provided between the cap cannula 213 and a surface of the access protrusion 212.

Figure 38:
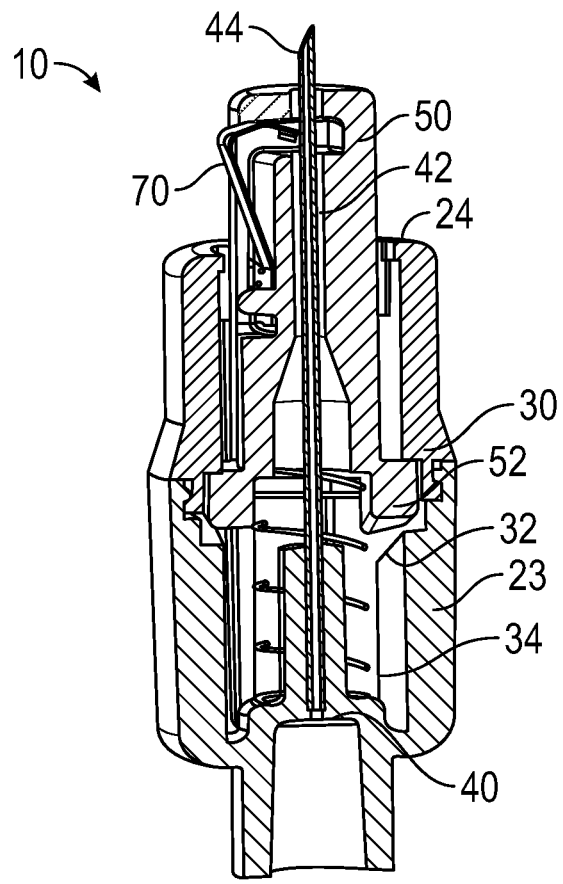
FIG. 38 is a cross-section of an exemplary safety needle device.

The caps disclosed herein are suitable for many different kinds of safety needle devices. FIG. 38 illustrates a cross-section of an exemplary tube-in-tube safety needle device 10 in a fill state. The safety features are guide elements (e.g., first, second, and third guide paths) for this exemplary safety needle device. The device has a housing body 23, and an opening 24 located on the distal end. A first guide path 30, a second guide path 32 and a third guide path 34 are disposed on the housing body 23. First guide path 30 and third guide path 34 are generally parallel to a central axis which extends along the housing body 23. Second guide path 32 is positioned at an angle, curvature or taper relative to the axis and intersects the first guide path 30 and third guide path 34 thereby serving to separate the first guide path 30 and third guide path 34. Second guide path 32 permits the guide element 52 to shift between the first guide path 30 and third guide path 34. In one or more embodiment, the first guide path 30, the second guide path 32 and the third guide path 34 are disposed on the inner diameter of the housing body 23 to prevent tampering. In one or more embodiment, the first guide path 30, the second guide path 32 and the third guide path 34 are disposed on the inner diameter of the housing body 23 so as not to obstruct needle cannula/needle tip visibility. A cap as disclosed herein is of a dimension that keeps the device in a fill state.

Figure 11:
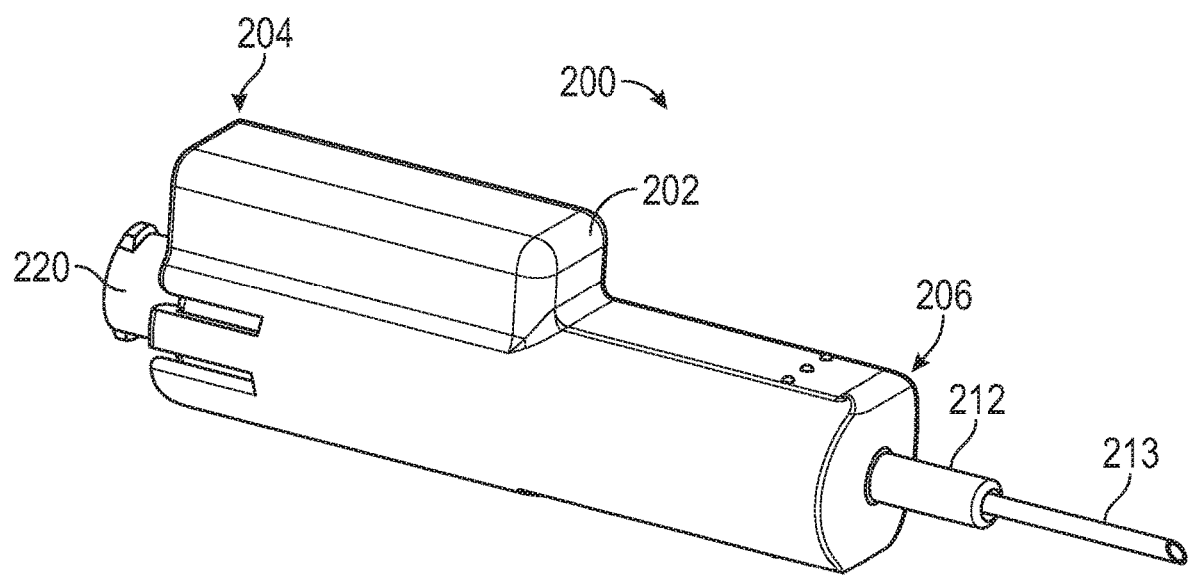
FIG. 11 provides a perspective view of a drug delivery safety device according to an embodiment.

FIG. 11 provides a perspective view of a drug delivery safety device according to an embodiment. Drug delivery device 200 comprises the cap 202 according to FIGS. 8-10 and 13 and a safety needle device 220, which has an activation latch ("stored energy latch") and is in an expanded configuration. The cap 202 removably attaches to a portion of the safety needle device 220 at a proximal end 204 of the cap 202. Cap cannula 213 resides in access protrusion 212 at a distal end 206 of the cap 202. The cap 202 may snap-fit, rotatably-fit, or press-fit to a portion of the safety needle device 220.

Figure 12:
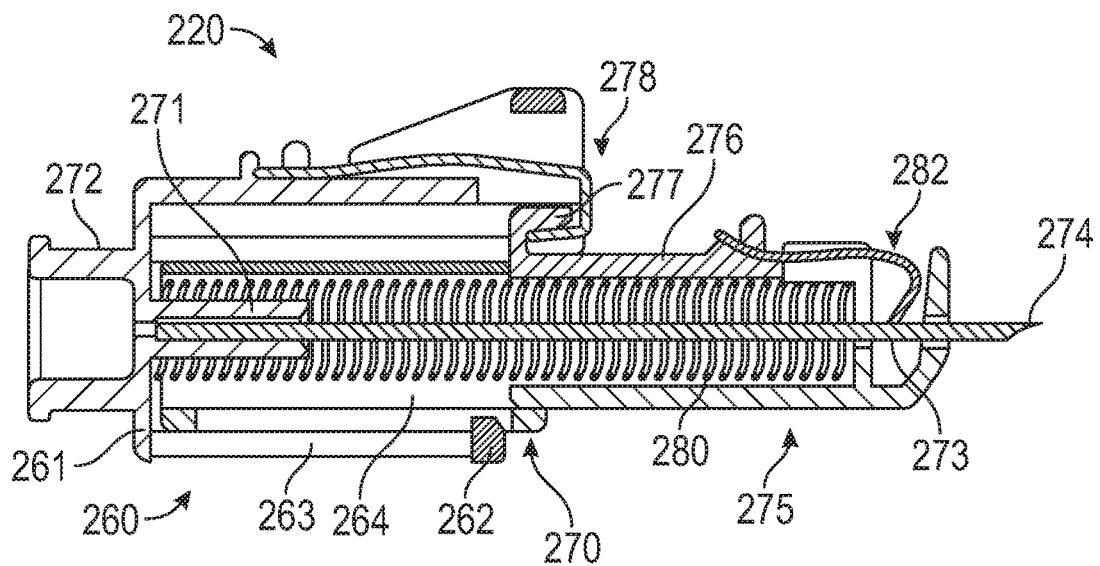
FIG. 12 provides a cross-section view of a safety needle device as included in FIG. 11.

FIG. 12 provides a cross-section view of a safety needle device as included in FIG. 11, which includes an activation latch. Safety needle device 220 includes a housing 260 configured to couple to a syringe (not shown), which has a proximal end 261, a distal end 262, a housing body 263 and an opening 264 located on the distal end 262. Tether 270 is disposed on the housing body 263. Tether 270 is generally parallel to a central axis which extends along the housing body 263.

Needle hub 272 is disposed on the proximal end 261 of the housing 260. Needle cannula 273 is attached to the needle hub 272. A needle support 271 extends from the needle hub 272 to support the needle cannula 273. Distal end 262 of housing 260 couples to a retractable sheath 275 such that the retractable sheath 275 is configured to move along a central axis in housing body 263. A channel and an aperture are included in the retractable sheath 275 in order to permit the needle cannula 273 and distal tip 274 of needle cannula 273 to pass therethrough.

A proximal end 276 of the retractable sheath 275 includes a retention hook 277 that extends radially outward from the proximal end 276 of retractable sheath 275 and is configured to engage an activation latch 278 of the housing body 263. Housing 260 has an opening that receives the retractable sheath 275. The retractable sheath 275 is spring loaded. Activation latch 278 and the spring element 280 hold stored energy. Upon beginning injection, the energy in the activation latch 278 is released once the retention hook 277 on the proximal end 276 of the retractable sheath 275 is released from engagement with the activation latch 278 upon a practitioner depressing the activation latch over a very short distance. A lockout latch 282 is able to clip over the distal tip 274 of the needle cannula 273 upon injection thereby passively locking out the safety needle device and preventing needle stick injury to the practitioner. Safety features of this safety needle device include but are not limited to the activation latch 278 and/or the lockout latch 282.

Figure 13:
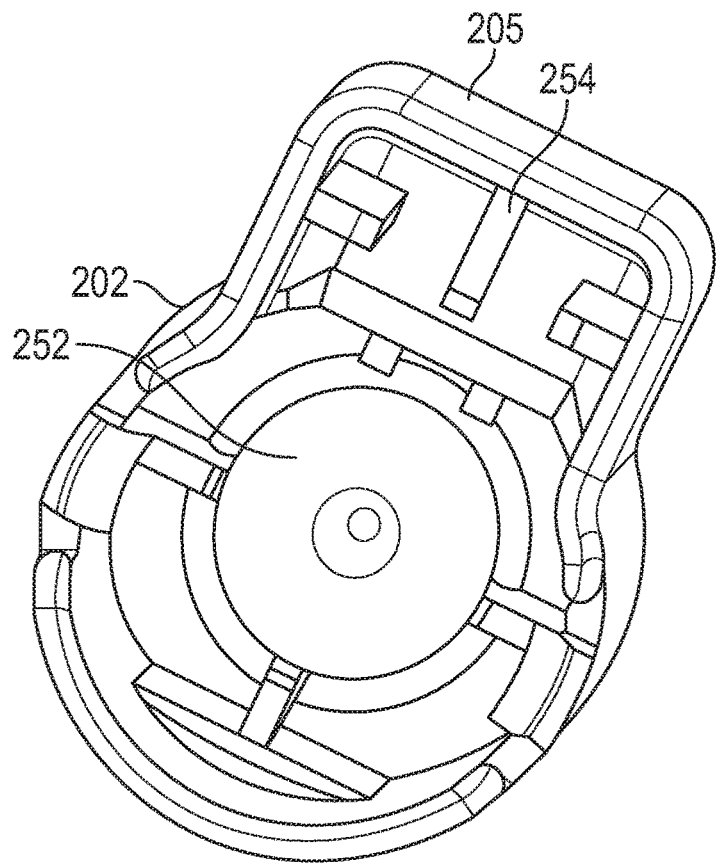
FIG. 13 is an interior view from a proximal end of a blunt fill needle cap as included in FIG. 11 to a distal end of the cap.

FIG. 13 is an interior view from the proximal end of the blunt fill needle cap 202, showing to a distal end of the cap, showing the septum 252 and fill feature 254. Fill feature 254 is a rib on an interior surface of the recess 205 of the cap 202. Fill feature 254 interacts with one or more activation latch safety features of the embodiment of FIG. 12 upon assembly to keep it in a fill state.

Figure 14:
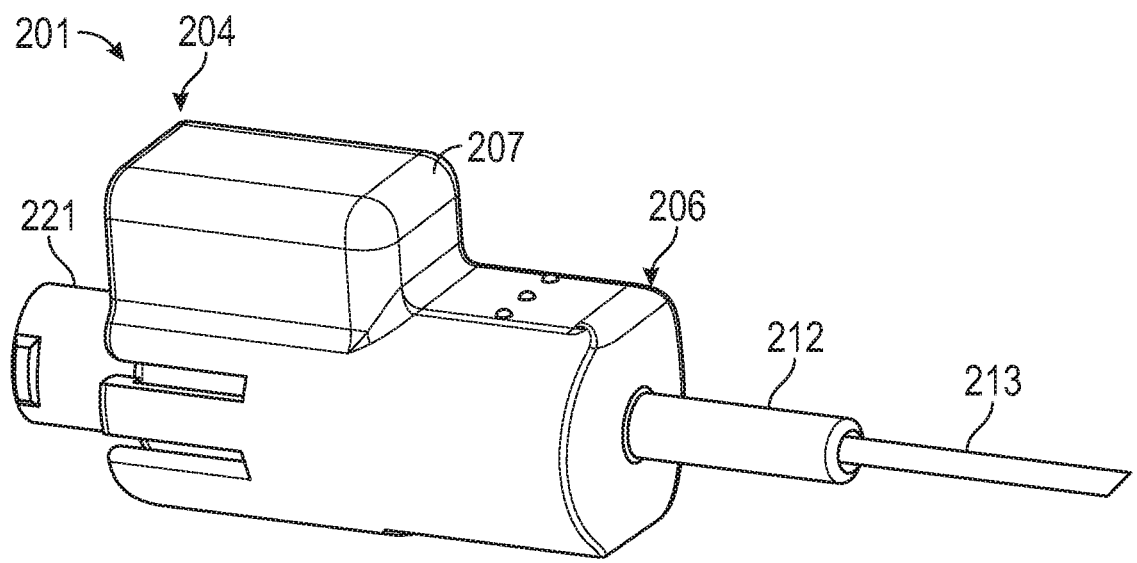
FIG. 14 provides a perspective view of a drug delivery safety device according to an embodiment.
Figure 15:
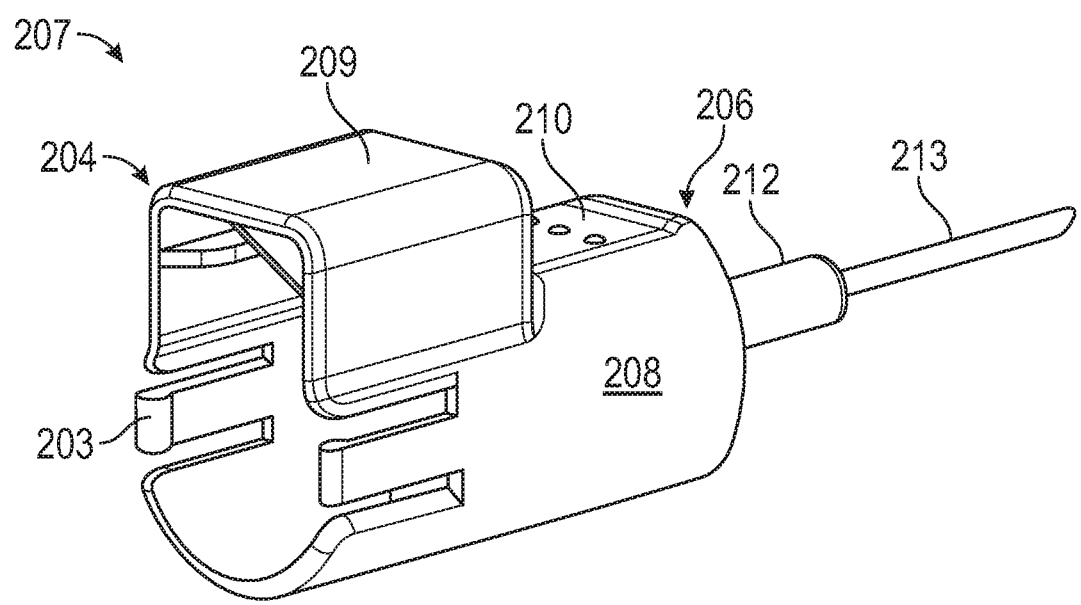
FIG. 15 is a perspective view of a blunt fill needle cap as included in FIG. 14.

FIG. 14 provides a perspective view of a drug delivery safety device according to an embodiment. FIG. 14 is analogous to FIG. 11 in terms of having a blunt fill needle cap in combination with a stored energy latch safety needle device. The stored energy latch safety needle device of FIG. 14 is provided in a compressed configuration. The blunt fill needle cap of FIGS. 14 and 15 are thereby shorter than those of FIGS. 11 and 8, respectively, but is analogous otherwise. Drug delivery device 201 comprises a cap 207 and a safety needle device 221, which has an activation latch ("stored energy latch") and is in a compressed configuration. The cap 207 removably attaches to a portion of the safety needle device 221 at a proximal end 204 of the cap 207. Cap cannula 213 resides in access protrusion 212 at a distal end 206 of the cap 202. The cap 207 may snap-fit, rotatably-fit, or press-fit to a portion of the safety needle device 221.

FIG. 15 provides a perspective view of a blunt fill needle cap 207 according to an embodiment. At a proximal end 204, there are one or more clips 203 for engaging with a portion of a needle safety device. The cap body 208 has a recess 209 for accommodating an underlying needle safety device in a compressed state having an activation latch. At a distal end 206 of the cap 207, there is a finger hilt 210. An access protrusion 212 extends from a shoulder of the cap 207. A cap cannula 213 extends from a distal end of the access protrusion 212. A mini-cap may be provided for the cap cannula 213. The cap 207 of this embodiment may be referred to as a blunt needle fill cap.

Figure 16:
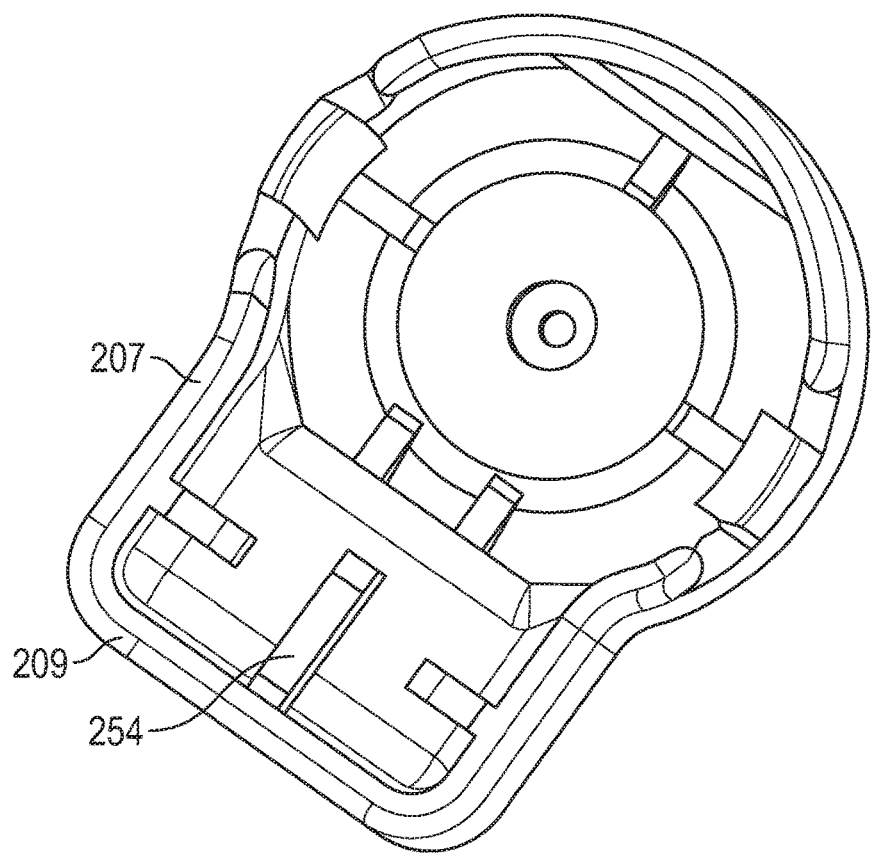
FIG. 16 is an interior view from a proximal end of the blunt fill needle cap of FIG. 15 to a distal end of the cap.

FIG. 16 is an interior view from a proximal end of the blunt fill needle cap of FIG. 15 to a distal end of the cap. FIG. 16 does not depict a septum but is otherwise analogous to FIG. 13 and in practice a septum is generally present. A fill feature 254 in the form of a rib interacts with one or more activation latch safety features of the safety needle device 221 of FIG. 14 upon assembly to keep it in a fill state.

Figure 17:
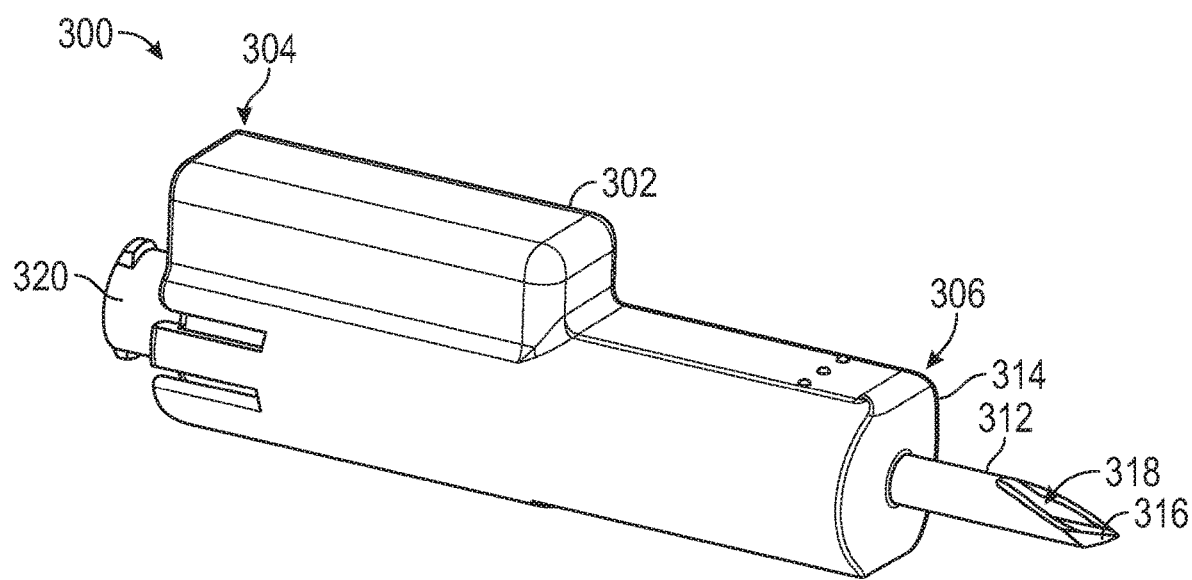
FIG. 17 provides a perspective view of a drug delivery safety device according to an embodiment.

FIG. 17 provides a perspective view of a drug delivery safety device according to an embodiment. FIG. 17 is analogous to FIG. 11 in terms of using a stored energy latch safety needle device in an expanded configuration. In FIG. 17, the cap is a spike cap, analogous to that of FIG. 1 for a different safety needle device. The spike cap of FIGS. 17 and 18 thereby have an addition of a recess to accommodate the activation latch. Drug delivery device 300 of FIG. 17 comprises cap 302 and a safety needle device 320, which has an activation latch ("stored energy latch") and is in an expanded configuration. The cap 302 removably attaches to a portion of the safety needle device 320 at a proximal end 304 of the cap 302. Shoulder 314 acts as a spike stop against a vial. There is a beveled tip 316 having an opening 318 at the end of the access protrusion 312, which is located at a distal end 306 of the cap 302. The cap 302 may snap-fit, rotatably-fit, or press-fit to a portion of the safety needle device 320.

Figure 18:
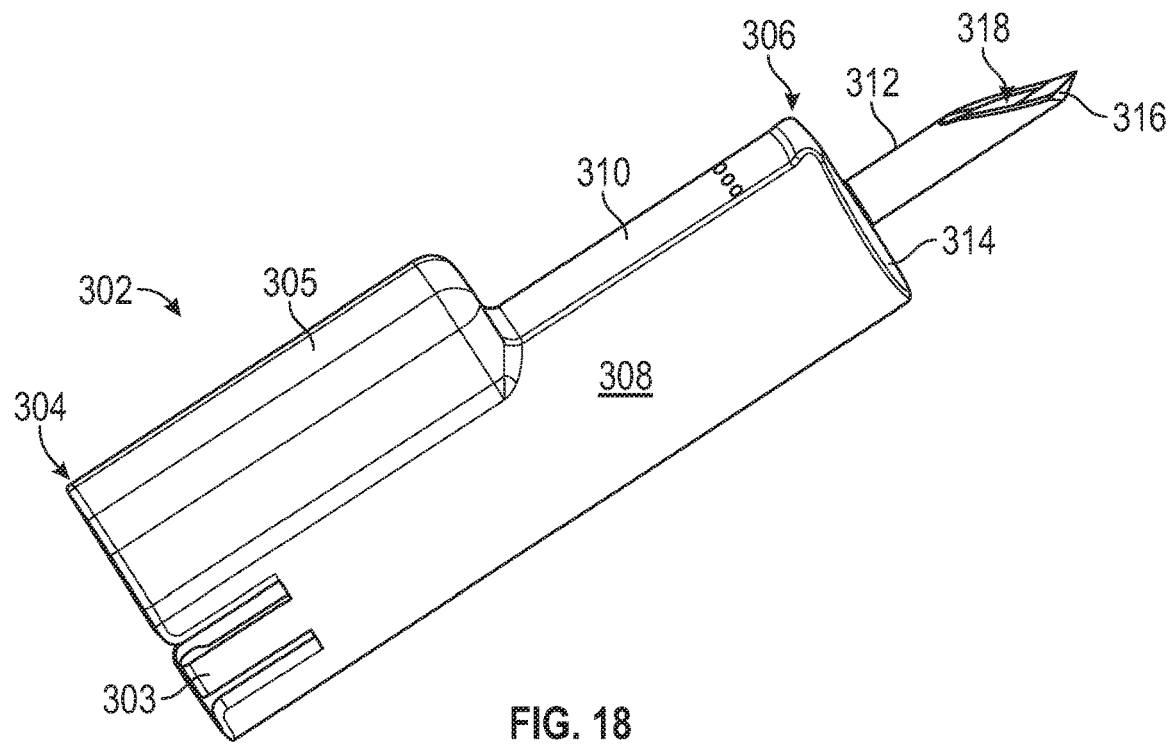
FIG. 18 is a perspective view of a spike cap as included in FIG. 17.

FIG. 18 provides a perspective view of the spike cap 302 according to an embodiment. At a proximal end 304, there are one or more clips 303 for engaging with a portion of a needle safety device. The cap body 308 has a recess 305 for accommodating an underlying needle safety device having an activation latch. At a distal end 306 of the cap 302, there is a finger hilt 310. The shoulder 314 acts as a spike stop against a vial. The beveled tip 316 has the opening 318 at the end of the access protrusion 312, which is located at the distal end 306 of the cap 302. A mini-cap may be provided for the beveled tip 316. The cap 302 of this embodiment may be referred to as spike cap.

Figure 19:
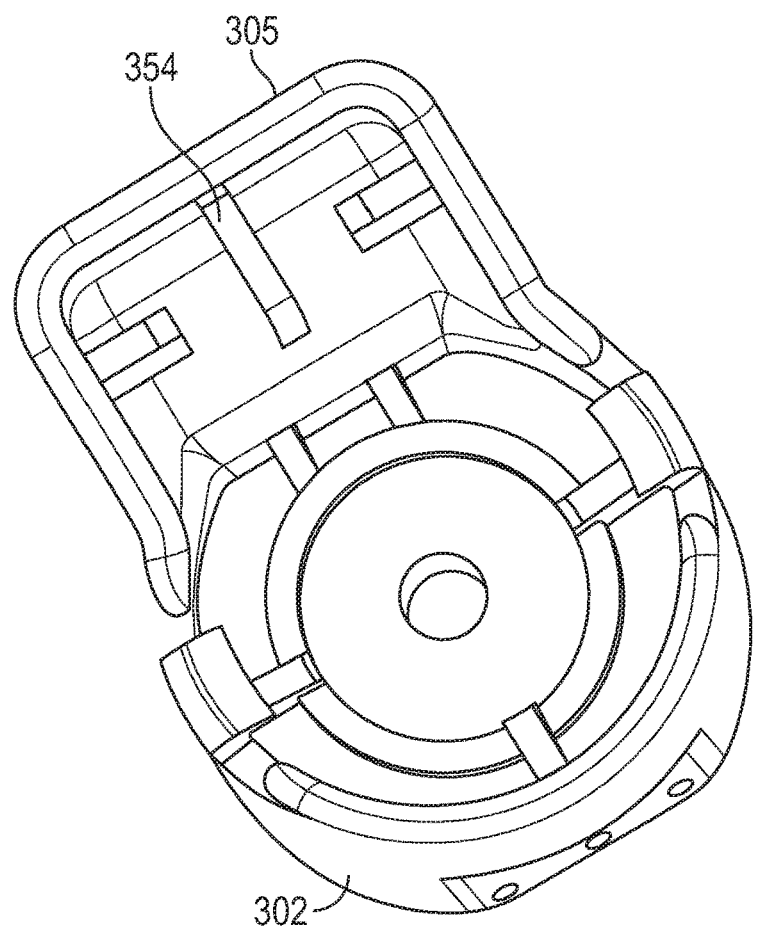
FIG. 19 is an interior view from a proximal end of the spike cap of FIG. 18 to a distal end of the cap.

FIG. 19 is an interior view from a proximal end of the spike cap of FIG. 18 to a distal end of the cap. FIG. 19 does not show a septum but is otherwise analogous to FIG. 13 and in practice a septum is generally present. A fill feature 354 in the form of a rib interacts with one or more the activation latch safety features of the safety needle device 320 of FIG. 17 upon assembly to keep it in a fill state.

Figure 20:
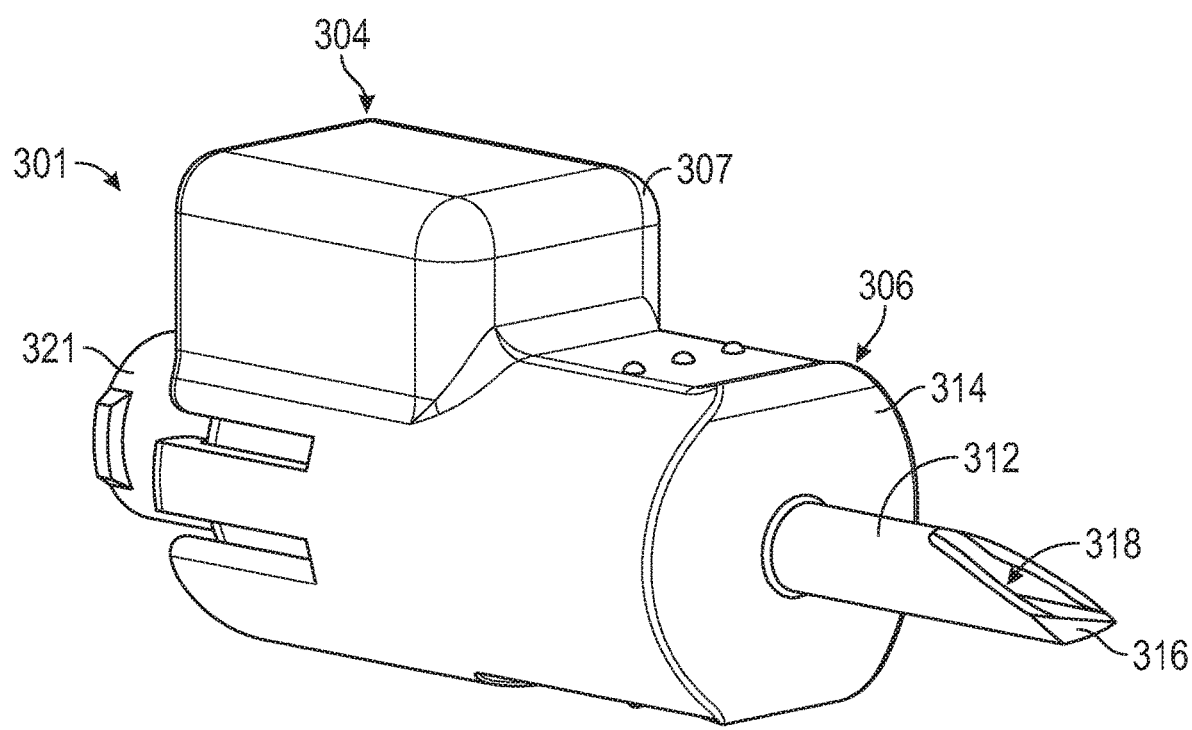
FIG. 20 provides a perspective view of a drug delivery safety device according to an embodiment.
Figure 21:
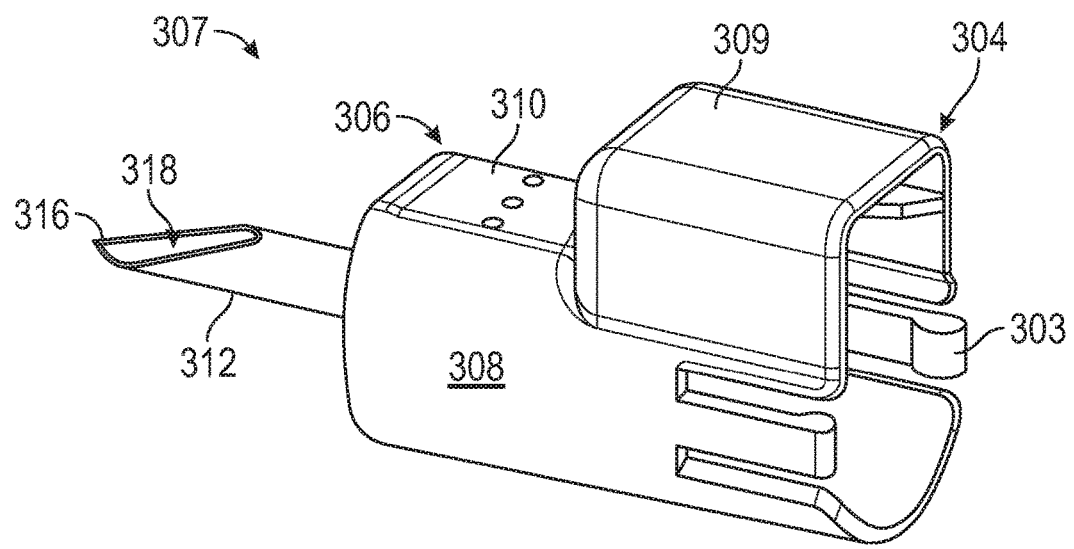
FIG. 21 is a perspective view of a spike cap as included in FIG. 20.

FIG. 20 provides a perspective view of a drug delivery safety device according to an embodiment. FIG. 20 is analogous to FIG. 14 in terms of using a stored energy latch safety needle device in a compressed state. FIGS. 20-21 include a spike cap analogous to that of FIG. 18 but is shorter in length. Drug delivery device 301 of FIG. 20 comprises a cap 307 and a safety needle device 321, which has an activation latch ("stored energy latch") and is in a compressed configuration. The cap 307 removably attaches to a portion of the safety needle device 321 at a proximal end 304 of the cap 307. Shoulder 314 acts as a spike stop against a vial. There is a beveled tip 316 having an opening 318 at the end of the access protrusion 312, which is located at a distal end 306 of the cap 307. The cap 307 may snap-fit, rotatably-fit, or press-fit to a portion of the safety needle device 321.

FIG. 21 provides a perspective view of the spike cap 307 according to an embodiment. At a proximal end 304, there are one or more clips 303 for engaging with a portion of a needle safety device. The cap body 308 has a recess 309 for accommodating an underlying needle safety device having an activation latch. At a distal end 306 of the cap 307, there is a finger hilt 310. The beveled tip 316 has the opening 318 at the end of the access protrusion 312, which is located at the distal end 306 of the cap 307. A mini-cap may be provided for the beveled tip 316. The cap 307 of this embodiment may be referred to as spike cap.

Figure 22:
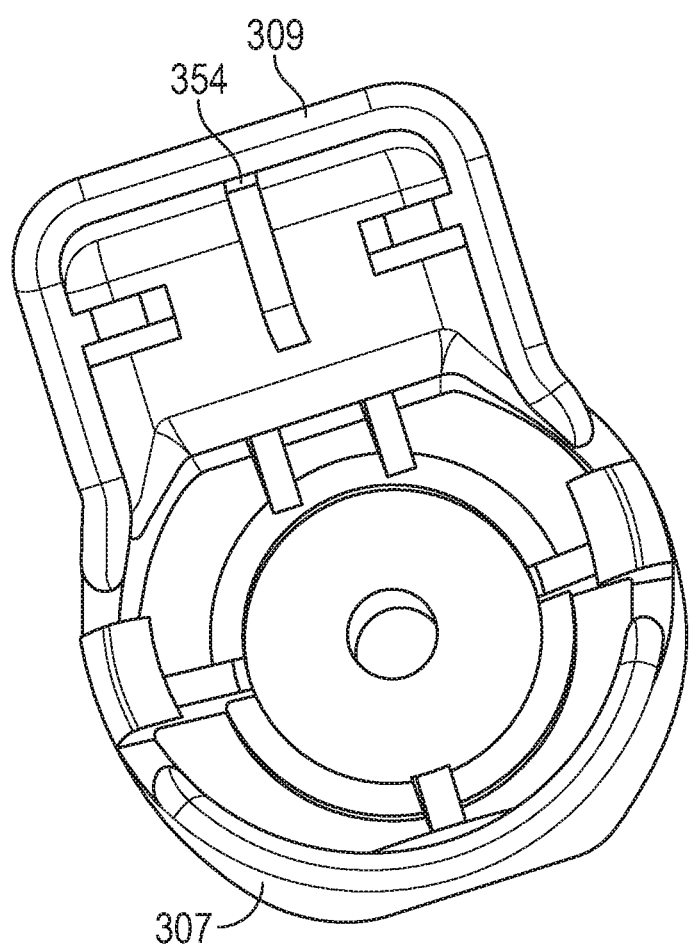
FIG. 22 is an interior view from a proximal end of the spike cap of FIG. 21 to a distal end of the cap.

FIG. 22 is an interior view from a proximal end of the spike cap of FIG. 21 to a distal end of the cap. FIG. 22 does not show a septum but is otherwise analogous to FIG. 13 and in practice a septum is generally present. A fill feature 354 in the form of a rib interacts with one or more activation latch safety features of the safety needle device 321 of FIG. 20 upon assembly to keep it in a fill state.

Figure 23:
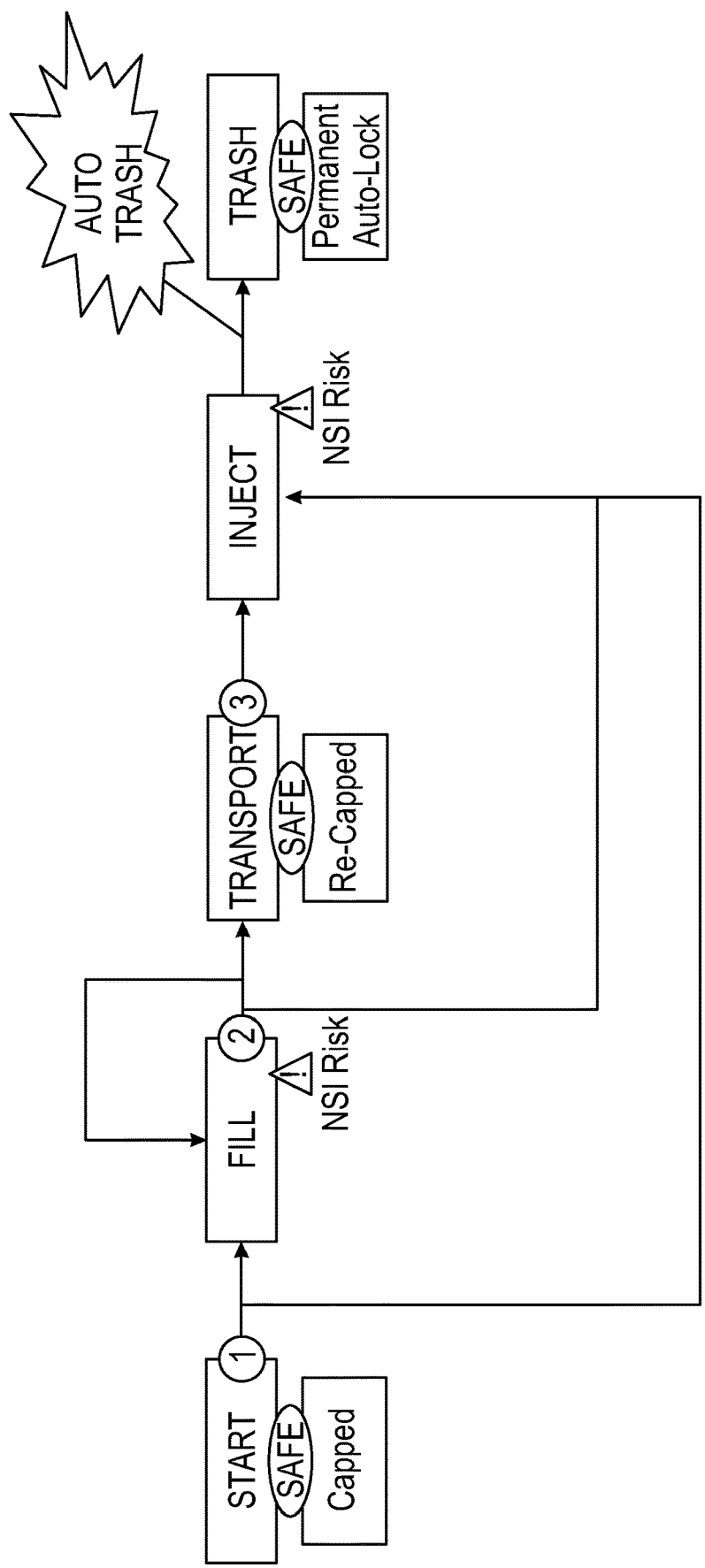
FIG. 23 is a general flow chart depicting "3 Choice" Passive Safety Device Functional Architecture.
Figure 24:
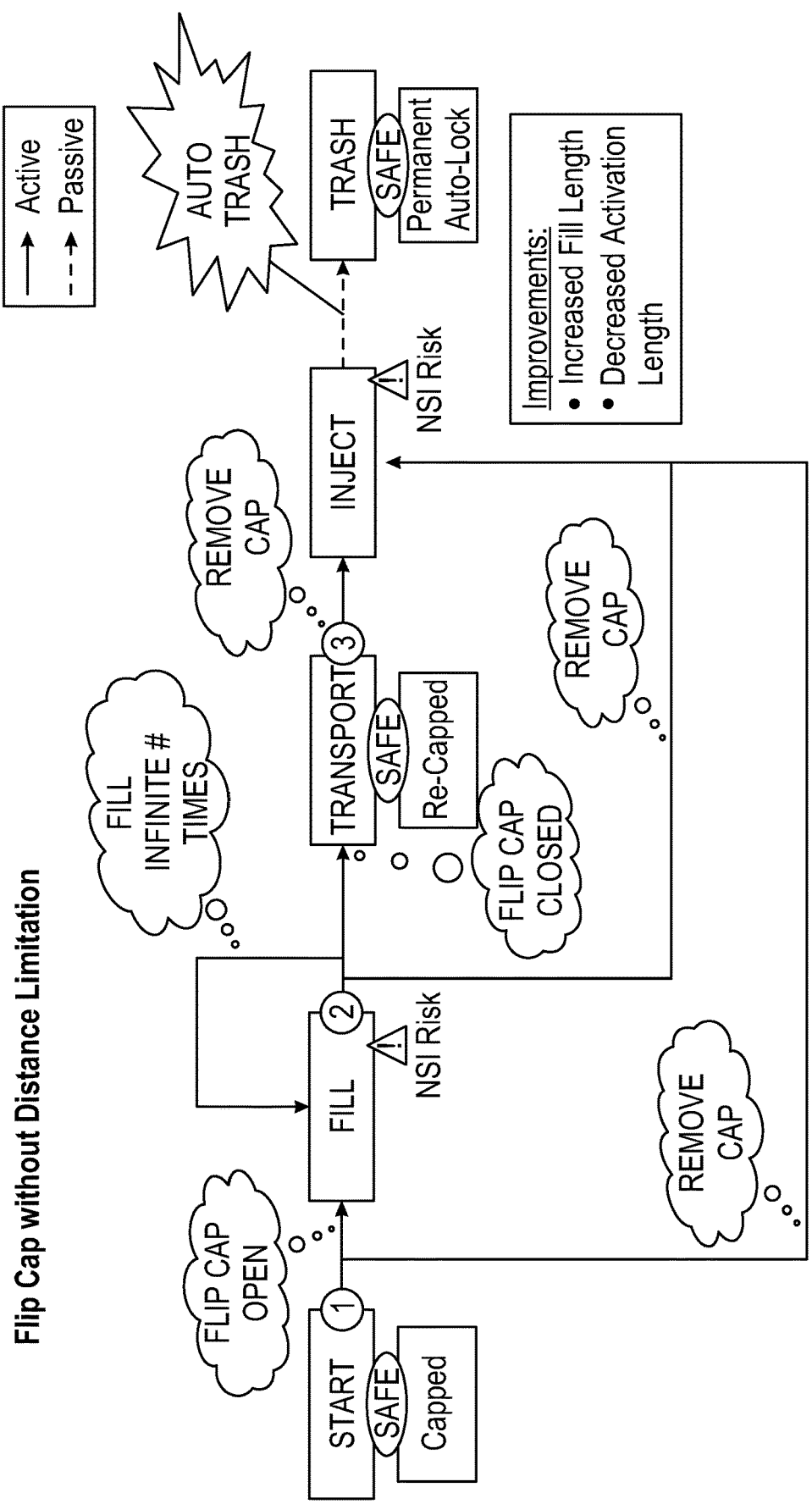
FIG. 24 is a flow chart depicting "3 Choice" for an embodiment.
Figure 25:
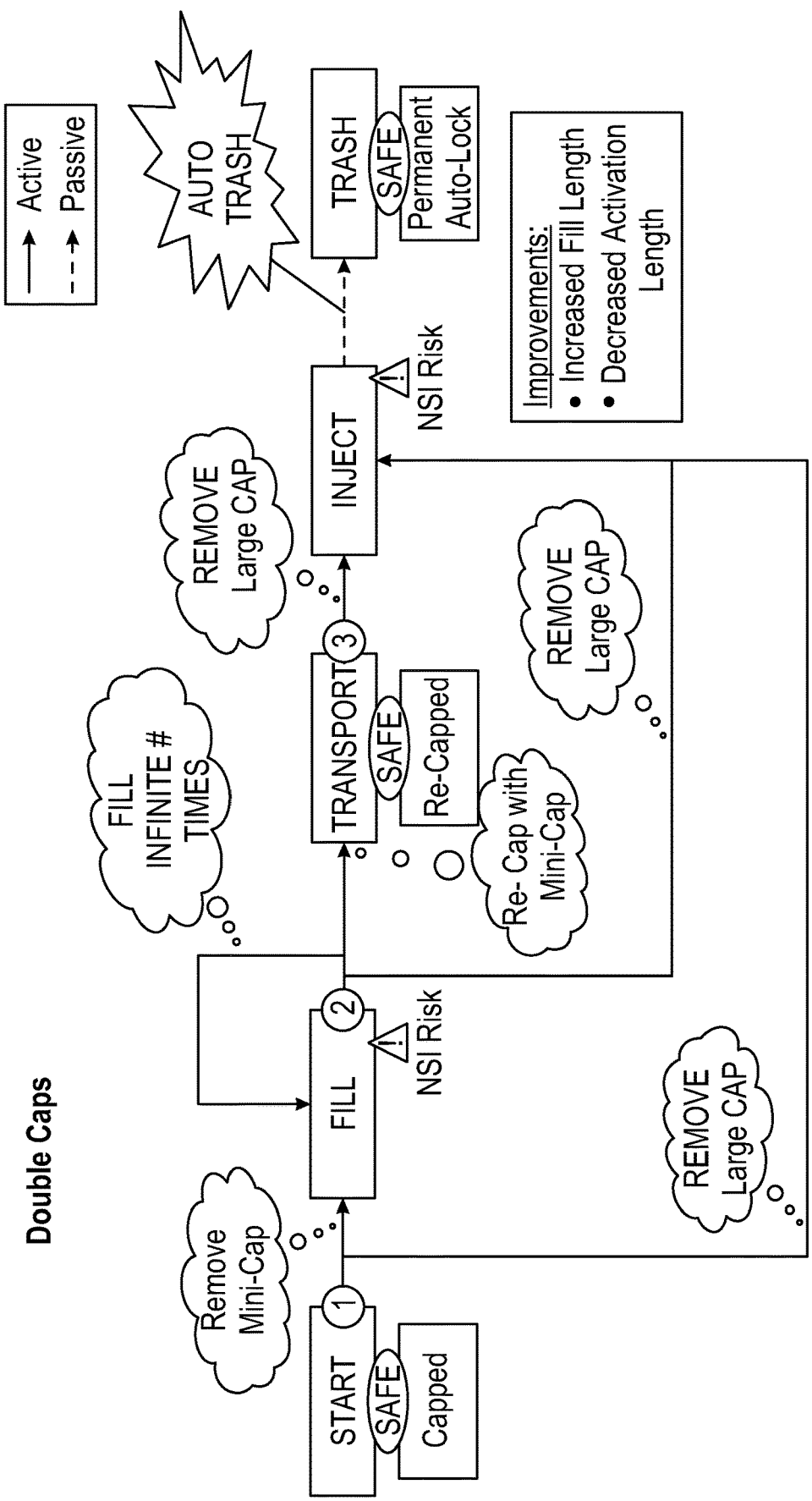
FIG. 25 is a flow chart depicting "3 Choice" for an embodiment.
Figure 26:
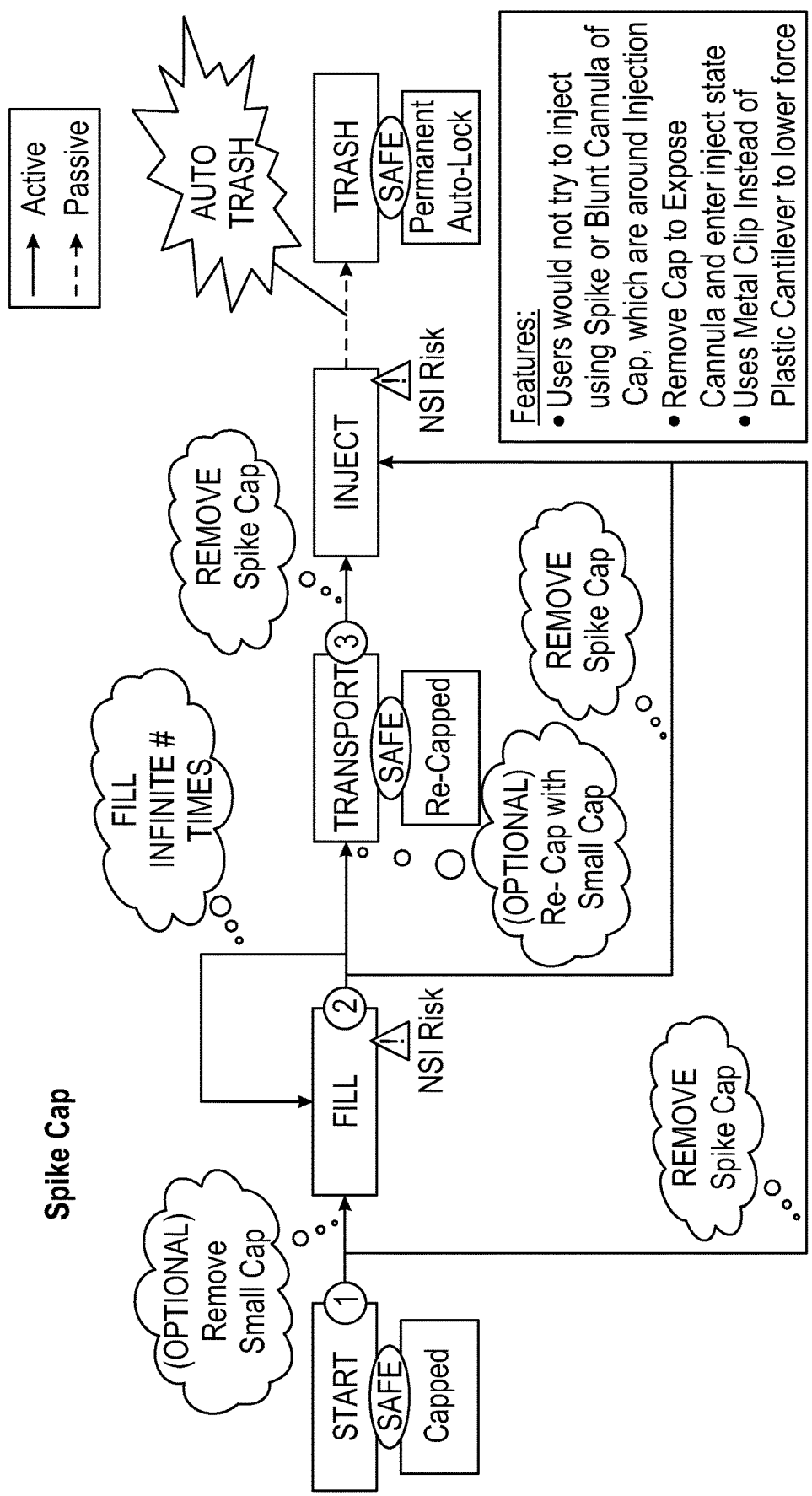
FIG. 26 is a flow chart depicting "3 Choice" for an embodiment.

FIG. 23 is a general flow chart depicting "3 Choice" Passive Safety Device Functional Architecture. FIG. 24 is a flow chart depicting "3 Choice" for an embodiment of using a flip cap without distance limitation. FIG. 25 is a flow chart depicting "3 Choice" for an embodiment of using double caps. FIG. 26 is a flow chart depicting "3 Choice" for an embodiment of using spike caps or blunt fill needle caps.

Figure 27:
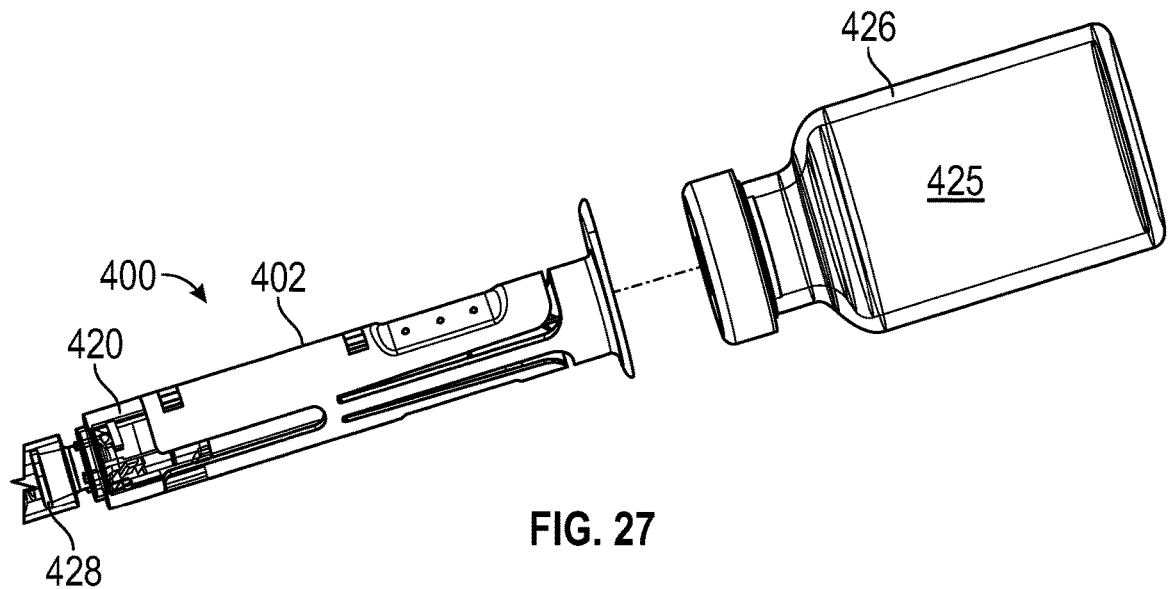
FIG. 27 is a perspective view of a drug delivery safety device before engaging with a vial.
Figure 28:
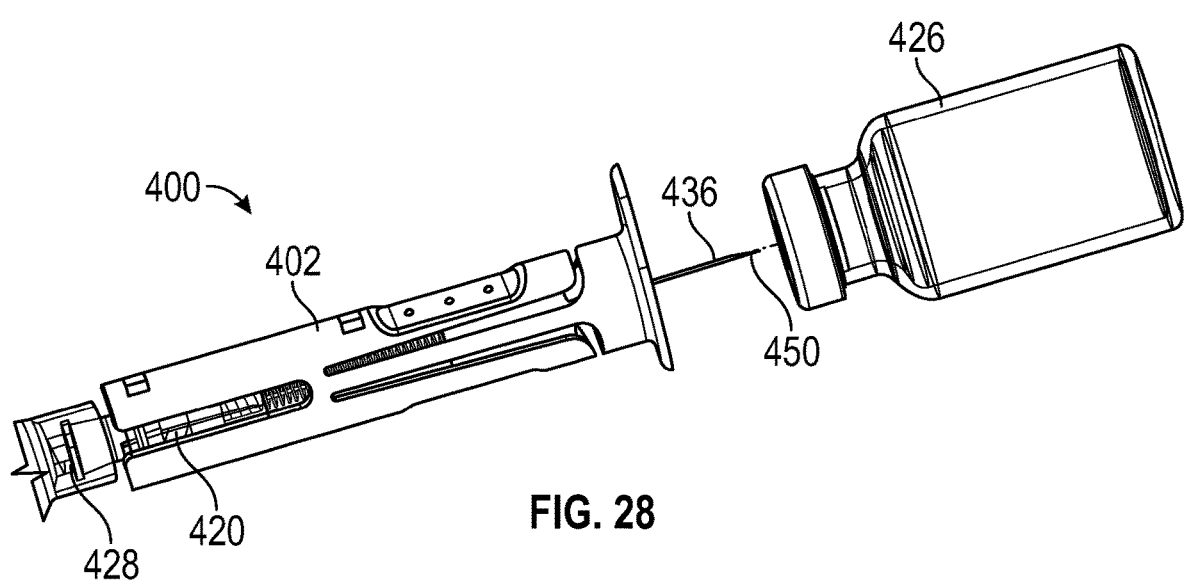
FIG. 28 is a perspective view of the drug delivery safety device of FIG. 27 after fill from a vial.
Figure 29:
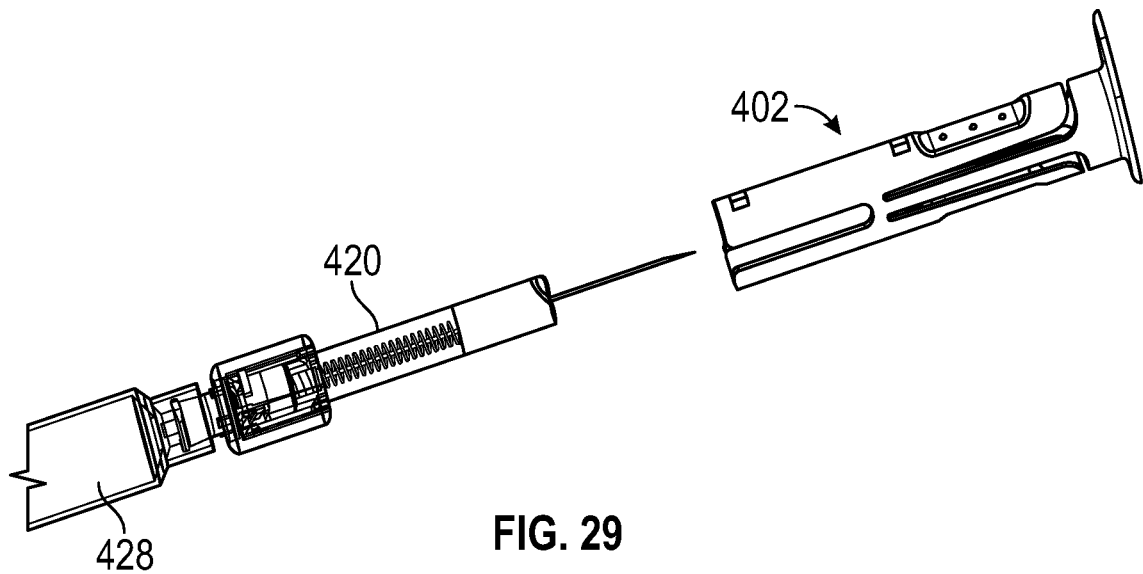
FIG. 29 is a perspective view of the drug delivery safety device of FIG. 27 after removal of the cap from safety needle device.

FIGS. 27-29 provide an embodiment referred to as a "clothes pin cap". This embodiment includes an internal rib to prevent safety locking during fill. No second cap is needed for 3 Choice Architecture. FIG. 27 is a perspective view of a drug delivery safety device 400 before engaging with a vial 426 of fluid 425. In FIG. 27, the cap 402 and safety needle device 420 are locked in start position. A cannula of safety needle device 420 is recessed in the cap 402 in FIG. 27. A syringe 428 is attached to a needle hub of the safety needle device 420, which is filled with fluid 425 from the vial 426. Low force (e.g., 0 lbs) is needed to push a vial off of the cap 402, which does not have an access protrusion and beveled tip of a spike cap; nor does it have an access protrusion and cap cannula of a blunt needle fill cap. FIG. 28 is a perspective view of the drug delivery safety device 400 of FIG. 27 after fill from a vial. To begin fill, the cap 402 is squeezed to pull it back and expose the cannula 436 through an access opening (not shown) of the cap 402, which may lock back or spring back. Distal tip 450 of the needle cannula 436 is inserted into vial 426. The cap 402 may be squeezed to pull off for injection, or rest back to start for transport, or can go straight to inject as well. Can have two discrete lock points, start-safe, retracted-inject, or act as a ratchet, such that the cap 402 can be moved axially while squeezed but locks when released. FIG. 29 is a perspective view of the drug delivery safety device 400 of FIG. 27 after removal of the cap 402 from safety needle device 420.

Figure 30:
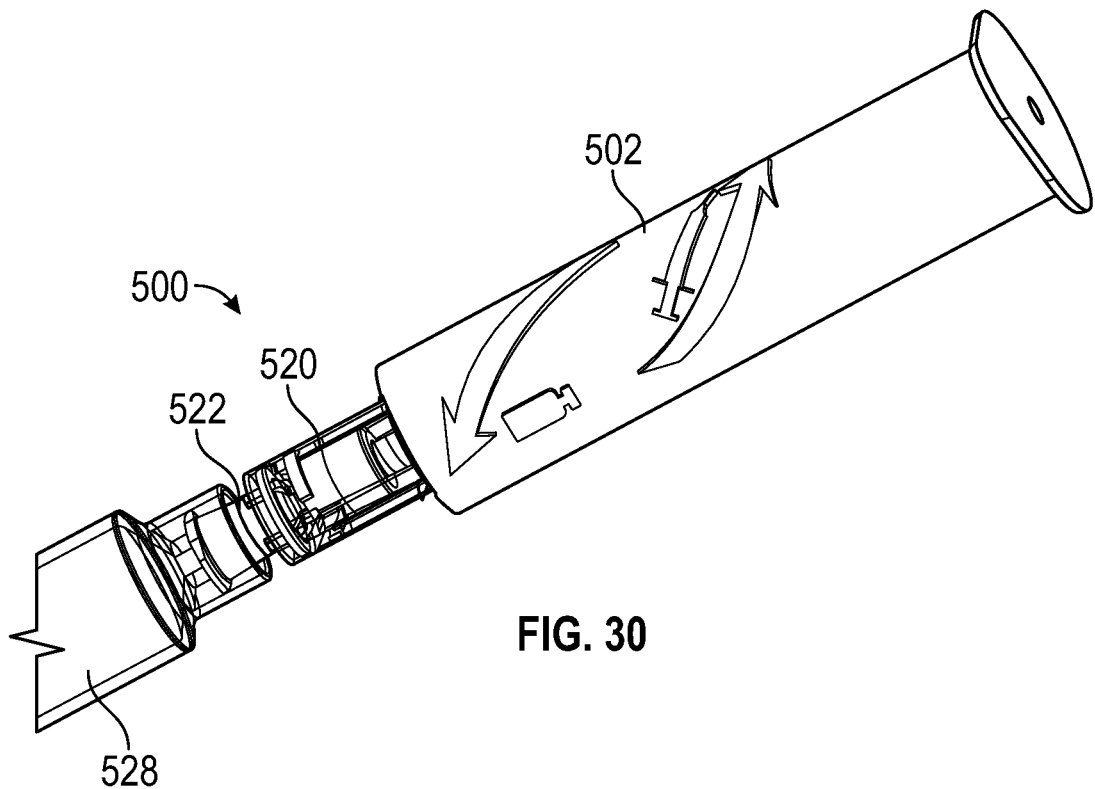
FIG. 30 is a perspective view of a drug delivery safety device according to an embodiment.
Figure 31:
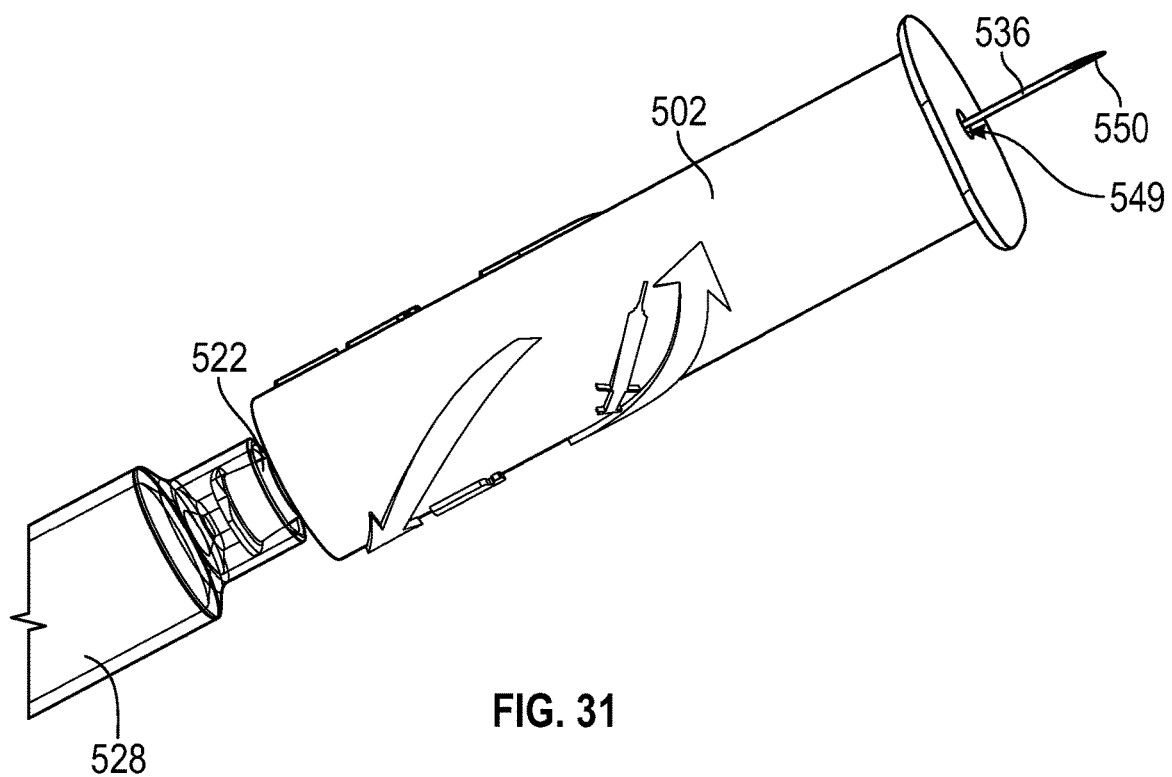
FIG. 31 is a perspective view of the drug delivery safety device of FIG. 30 in a fill state.
Figure 32:
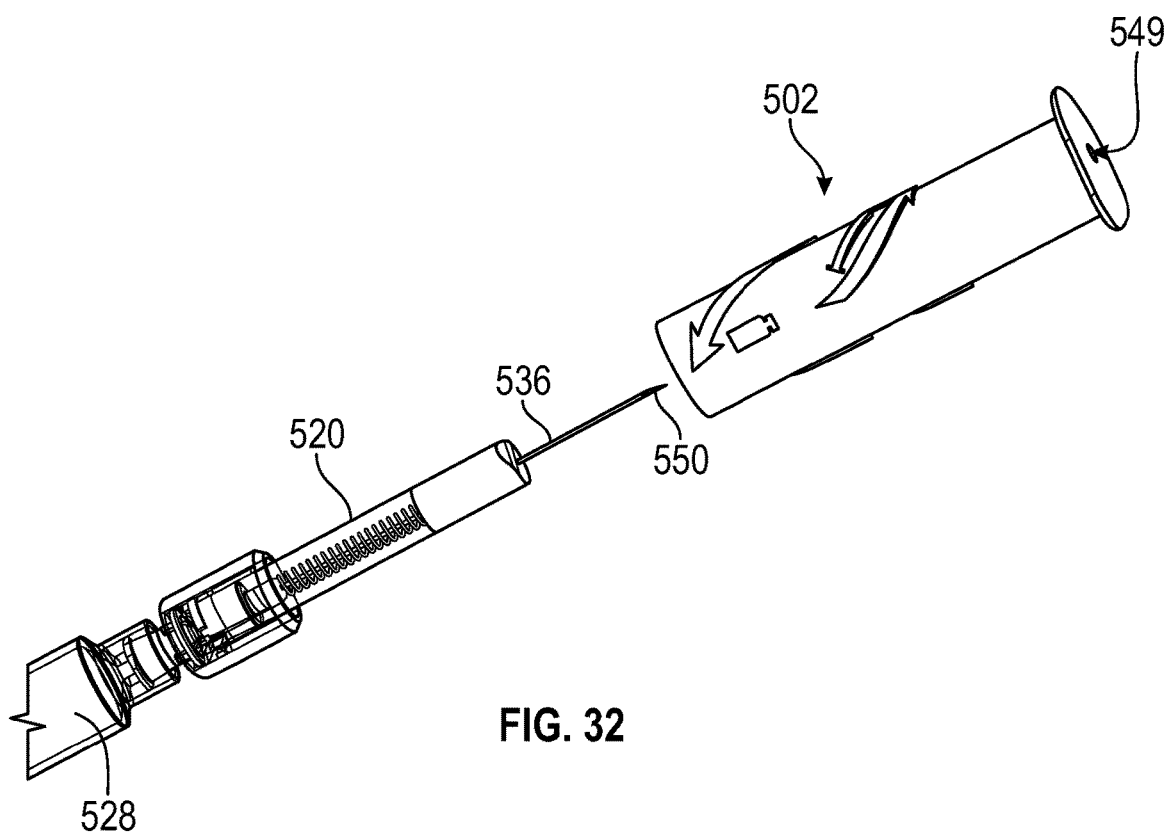
FIG. 32 is a perspective view of the drug delivery safety device of FIG. 30 after removal of the cap from safety needle device.

FIGS. 30-32 provide an embodiment referred to as a "twist cap". An internal helix rib prevents safety locking during fill. No second cap is needed for 3 Choice Architecture. FIG. 30 is a perspective view of a drug delivery safety device 500 before engaging with a vial, where cap 502 and safety needle device 520 are locked in a start position. A cannula of safety needle device 420 is recessed in the cap 402 in FIG. 29. A syringe 528 is attached to a needle hub 422 of the safety needle device 520. Low force (e.g., 0 lbs) is needed to push a vial off of the cap 502, which does not have an access protrusion and beveled tip of a spike cap; nor does it have an access protrusion and cap cannula of a blunt needle fill cap. FIG. 31 is a perspective view of the drug delivery safety device 500 of FIG. 30 in a fill state. To begin fill, the cap 502 is twisted to pull back and expose the cannula 536 through an access opening 549 of the cap 502, which locks back (helix cannot be back driven). Distal tip 550 of the needle cannula 536 is inserted into a vial. The cap 502 may twist off for inject, or reset back to start (detented) for transport, can go straight to inject as well. No compound motion is needed as in the above clothspin cap. Only a twist is needed to change cap state. The cap helix can have sufficient pitch to prevent axial back-driving, this prevents bumps to the cap from exposing the sharp. FIG. 32 is a perspective view of the drug delivery safety device 500 of FIG. 30 including access opening 549 after removal of the cap 502 from safety needle device 420 including cannula 536 and distal top 550.

Figure 33:
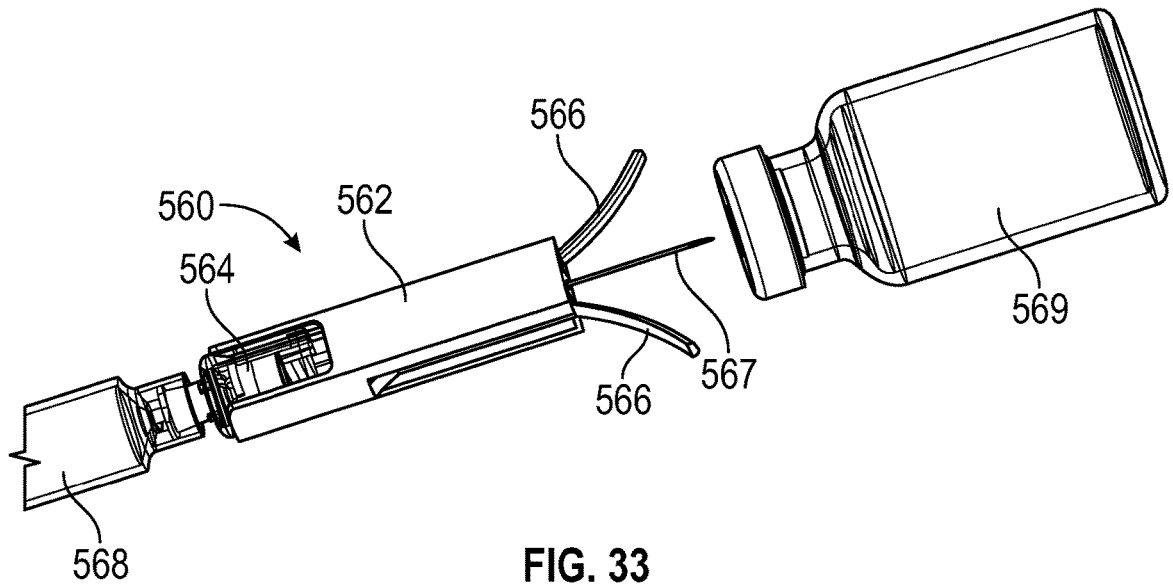
FIG. 33 is a perspective view of a drug delivery safety device according to an embodiment in a fill state.

FIG. 33 provides a drug delivery safety device 560 comprising a cap 562 referred to as a "basket cap with flex arms," which is attached to a safety needle device 564, which is attached to a syringe 568. This embodiment includes an internal rib to prevent safety locking during fill. A second cap is needed. Cannula 567 of the safety needle device 564 is exposed for insertion into vial 569. The cannula 567 of the safety needle device 564 passes though through an access opening (not shown) of the cap 562. Arms 566 reduce chance of inject in fill state because arms 566 will contact skin of a patient. Arms 566 flex open for vial 569 however.

Figure 34:
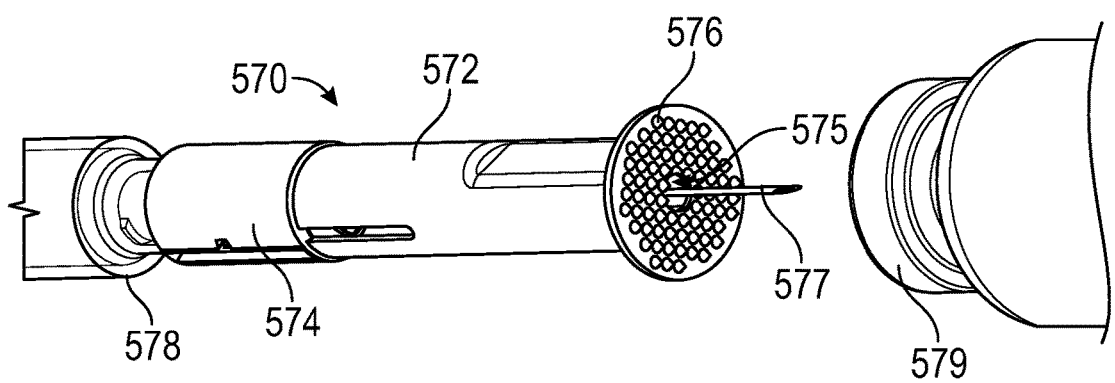
FIG. 34 is a perspective view of a drug delivery safety device according to an embodiment in a fill state.

FIG. 34 provides a drug delivery safety device 570 comprising a cap 572 referred to as a "spikey cap," which is attached to a safety needle device 574, which is attached to a syringe 578. This embodiment includes an internal rib to prevent safety locking during fill. A second cap is needed. Cannula 577 of the safety needle device 574 passes though through an access opening 575 of the cap 572 for insertion into vial 579. A plurality of spikes 576 reduce chance of inject in fill state. Spikes 577 will contact skin of a patient and cause negative feedback, but act as stabilizer for rubber stopper. The visual appearance of the spikes may prevent the user from contacting a patient's skin.

Figure 35:
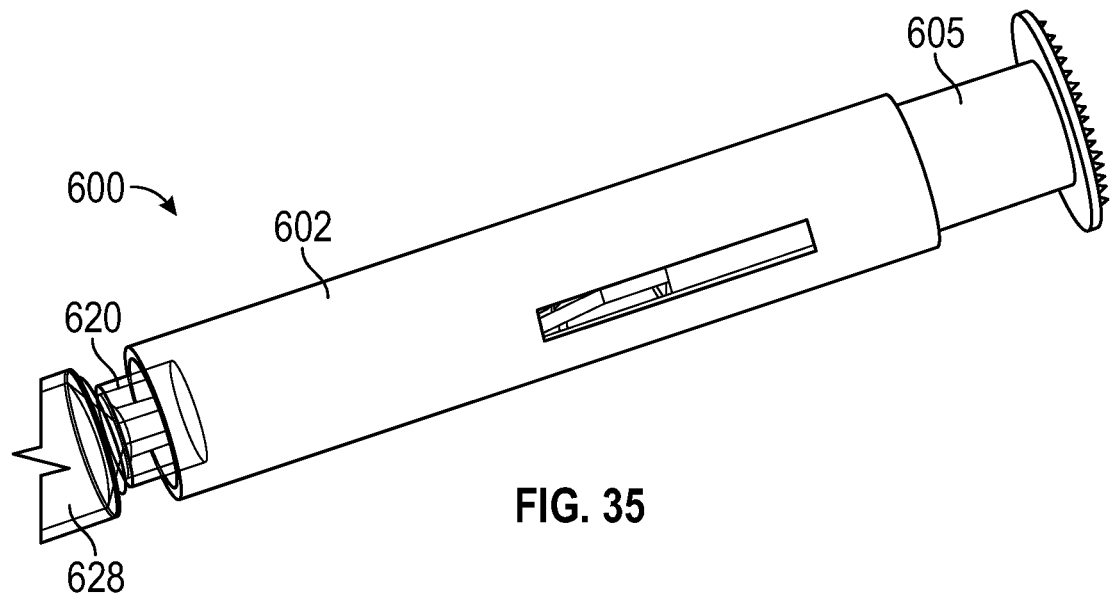
FIG. 35 is a perspective view of a cap according to an embodiment.
Figure 36:
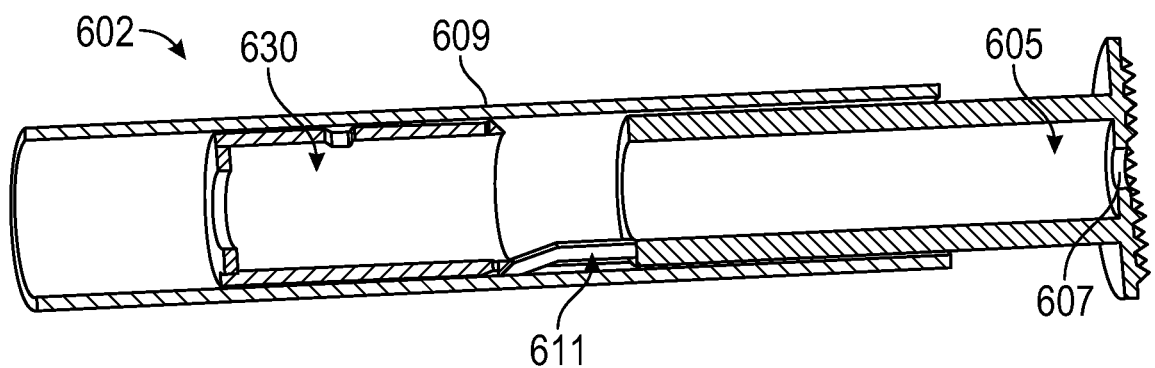
FIG. 36 is a cross-section view of the cap of FIG. 35.

FIGS. 35-36 provide an embodiment referred to as a "collet cap." FIG. 35 is a perspective view of a drug delivery safety device 600 comprising a cap 602 and a safety needle device 620. A shield face 605 of the cap 602 covers a cannula of safety needle device 620. The safety needle device 620 is attached to a syringe 628. A second cap is needed. FIG. 36 is a cross-section view of the cap 602 of FIG. 35. Cap 602 comprises the shield face 605, which comprises an access opening 607. A cannula is exposed and free to move through access opening 607 by pulling back on a collet 609, which is effectively the outer diameter (OD) of the cap 602. Motion of collet 609 against a device body 630 (of safety needle device 620 of FIG. 34) flexes lock arms 611 open. Bumping the distal end of the cap 602 does not retract the cap 602, only pulling on the collet 609 does, this prevents unintended needle exposure.

Figure 37:
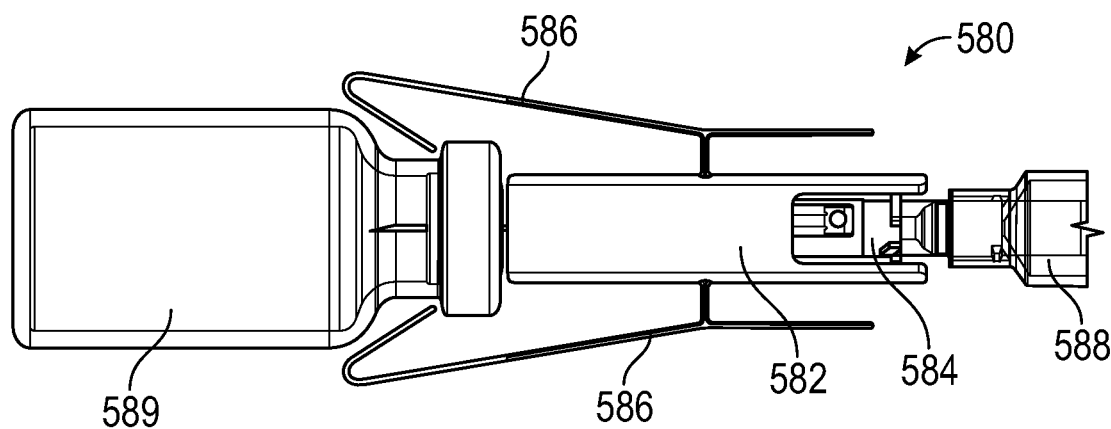
FIG. 37 is a perspective view of a drug delivery safety device according to an embodiment in a fill state engaged with a vial.

FIG. 37 provides a drug delivery safety device 580 comprising a cap 582 referred to as a "cap with grip arms," which is attached to a safety needle device 584, which is attached to a syringe 588. A second cap is needed. A cannula of the safety needle device 584 passes though through an access opening (not shown) of the cap 582. Grip arms 586 reduce chance of inject in fill state because arms 586 will contact skin of a patient. Grip arms 586 flex open for vial 589 however and grip a neck of the vial 589 for stability.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A drug delivery safety device comprising:
   a safety needle device comprising a needle hub, a needle cannula, and a safety feature; and
   a cap comprising a cap body having a proximal end attached to the safety needle device and a distal end having an access opening that is in fluid communication with the needle cannula, the access opening comprises an access protrusion extending from the distal end of the cap, the cap further comprises a blunt fill cannula extending from a distal end of the access protrusion and in fluid communication with the needle cannula and a seal between the blunt fill cannula and an inside surface of the access protrusion.

2. The drug delivery safety device of claim 1, wherein the proximal end of the cap is removably attached to the safety needle device.

3. The drug delivery safety device of claim 1, wherein an inside surface of the cap further comprises a fill feature engagable with the safety needle device for maintaining a fill state of the safety needle device.

4. The drug delivery safety device of claim 3, wherein the fill feature comprises a rib located on the inside surface of the cap body in contact with the safety feature of the safety needle device.

5. The drug delivery safety device of claim 4, wherein the safety feature of the safety needle device comprises an activation latch and the rib keeps the activation latch in an inactive state.

6. The drug delivery safety device of claim 3, wherein the safety feature of the safety needle device comprises a clip and the fill feature keeps the clip open in an inactive state.

7. The drug delivery safety device of claim 1, wherein the safety feature comprises a guide element of a housing body of the safety needle device.

8. The drug delivery safety device of claim 1, wherein the cap snap-fits to the safety needle device.

9. The drug delivery safety device of claim 1, wherein the cap rotatably-fits to the safety needle device.

10. The drug delivery safety device of claim 1, wherein the cap press-fits to the safety needle device.

11. The drug delivery safety device of claim 1, wherein the proximal end of the cap is attached to the needle hub of the safety needle device.

12. The drug delivery safety device of claim 1, wherein the cap further comprises a septum inside the cap body at the distal end adjacent to the access opening and optionally a vent lumen.

13. The drug delivery safety device of claim 1, wherein the cap further comprises a finger hilt.

14. The drug delivery safety device of claim 1, wherein the cap further comprises a shoulder at the distal end of the cap body from which the access protrusion extends.

15. The drug delivery safety device of claim 1 further comprising a tip cap that covers a tip of the blunt fill cannula.

\* \* \* \* \*